(12) United States Patent
Jewett et al.

(10) Patent No.: US 10,577,632 B2
(45) Date of Patent: Mar. 3, 2020

(54) CELL-FREE PROTEIN SYNTHESIS DRIVEN METABOLIC ENGINEERING FOR THE PRODUCTION OF 1-BUTANOL

(71) Applicant: Northwestern University, Evanston, IL (US)

(72) Inventors: Michael Christopher Jewett, Evanston, IL (US); Ashty Stephen Karim, Chicago, IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 15/175,497

(22) Filed: Jun. 7, 2016

(65) Prior Publication Data

US 2016/0362708 A1    Dec. 15, 2016

Related U.S. Application Data

(60) Provisional application No. 62/173,818, filed on Jun. 10, 2015.

(51) Int. Cl.
*C12P 7/16* (2006.01)

(52) U.S. Cl.
CPC ..................................... *C12P 7/16* (2013.01)

(58) Field of Classification Search
CPC combination set(s) only.
See application file for complete search history.

(56) References Cited

U.S. PATENT DOCUMENTS

| | | | |
|---|---|---|---|
| 8,357,529 B2 | 1/2013 | Swartz et al. |
| 2004/0209321 A1 | 10/2004 | Swartz et al. |
| 2007/0154983 A1 | 7/2007 | Calhoun et al. |
| 2016/0060301 A1 | 3/2016 | Jewett et al. |
| 2018/0016614 A1 | 1/2018 | Jewett et al. |

OTHER PUBLICATIONS

Atsumi, S. et al. Metabolic engineering of *Escherichia coli* for 1-butanol production. Metabolic engineering 10, 305-311, doi:10.1016/j.ymben.2007.08.003 (2008).
Bogorad, I.W., Lin, T. S. & Liao, J. C. Synthetic non-oxidative glycolysis enables complete carbon conservation. Nature 502, 693-697, doi:10.1038/nature12575 (2013).
Bond-Watts, B. B., Bellerose, R. J. & Chang, M. C. Enzyme mechanism as a kinetic control element for designing synthetic biofuel pathways. Nature chemical biology 7, 222-227, doi:10.1038/nchembio.537 (2011).
Bornscheuer, U. T. et al. Engineering the third wave of biocatalysis. Nature 485, 185-194, doi:10.1038/nature11117 (2012).
Boyle, P. M. & Silver, P. A. Parts plus pipes: synthetic biology approaches to metabolic engineering. Metabolic engineering 14, 223-232, doi:10.1016/j.ymben.2011.10.003 (2012).
Bujara, M., Schumperli, M., Pellaux, R., Heinemann, M. & Panke, S. Optimization of a blueprint for in vitro glycolysis by metabolic real-time analysis. Nat Chem Biol 7, 271-277, doi:10.1038/nchembio.541 (2011).
Carlson, E. D., Gan, R., Hodgman, C. E. & Jewett, M. C. Cell-free protein synthesis: applications come of age. Biotechnology advances 30, 1185-1194, doi:10.1016/j.biotechadv.2011.09.016 (2012).
Curran, K. A. & Alper, H. S. Expanding the chemical palate of cells by combining systems biology and metabolic engineering. Metabolic engineering 14, 289-297, doi:10.1016/j.ymben.2012.04.006 (2012).
Dai, Z. & Nielsen, J. Advancing metabolic engineering through systems biology of industrial microorganisms. Current opinion in biotechnology 36, 8-15, doi:10.1016/j.copbio.2015.08.006 (2015).
Daugherty, A. B., Govindarajan, S. & Lutz, S. Improved biocatalysts from a synthetic circular permutation library of the flavin-dependent oxidoreductase old yellow enzyme. J Am Chem Soc 135, 14425-14432, doi:10.1021/ja4074886 (2013).
Demain, A. L. Importance of microbial natural products and the need to revitalize their discovery. Journal of industrial microbiology & biotechnology 41, 185-201, doi:10.1007/s10295-013-1325-z (2014).
Dodevski, I., Markou, G. C. & Sarkar, C. A. Conceptual and methodological advances in cell-free directed evolution. Curr Opin Struct Biol 33, 1-7, doi:10.1016/j.sbi.2015.04.008 (2015).
Dong, H. et al. Engineering *Escherichia coli* Cell Factories for n-Butanol Production. Advances in biochemical engineering/biotechnology, doi:10.1007/10_2015_306 (2015).
Dudley Q. M. Karim, A. S. & Jewett, M. C. Cell-free metabolic engineering: biomanufacturing beyond the cell. Biotechnology journal 10, 69-82, doi:10.1002/biot.201400330 (2015).
Erickson, B., Nelson & Winters, P. Perspective on opportunities in industrial biotechnology in renewable chemicals. Biotechnology journal 7, 176-185, doi:10.1002/biot.201100069 (2012).
Fritz, B. R., Timmerman, L. E., Daringer, N. M., Leonard, J. N. & Jewett, M. C. Biology by design: from top to bottom and back. Journal of biomedicine & biotechnology 2010, 232016, doi:10.1155/2010/232016 (2010).
Green, E. M. Fermentative production of butanol—the industrial perspective. Current opinion in biotechnology 22, 337-343, doi:10.1016/j.copbio.2011.02.004 (2011).
Goshima, N. et al. Human protein factory for converting the transcriptome into an in vitro-expressed proteome. Nature Methods 5, 1011-1017, doi:10.1038/nmeth.1273 (2008).
Gulevich, A. Y., Skorokhodova, A. Y., Sukhozhenko, A. V., Shakulov, R. S. & Debabov, V. G. Metabolic engineering of *Escherichia coli* for 1-butanol biosynthesis through the inverted aerobic fatty acid beta-oxidation pathway. Biotechnol Lett 34, 463-469, doi:10.1007/s10529-011-0797-z (2012).
Guterl, J. K. et al. Cell-free metabolic engineering: production of chemicals by minimized reaction cascades. ChemSusChem 5, 2165-2172, doi:10.1002/cssc.201200365 (2012).
Harvey, A. L., Edrada-Ebel, R. & Quinn, R. J. The re-emergence of natural products for drug discovery in the genomics era. Nature reviews. Drug discovery 14, 111-129, doi:10.1038/nrd4510 (2015).

(Continued)

*Primary Examiner* — Kagnew H Gebreyesus
(74) *Attorney, Agent, or Firm* — Quarles & Brady LLP; M. Scott McBride

(57) ABSTRACT

Disclosed are cell-free systems for metabolic engineering, methods for cell-free metabolic engineering, kits for preparing the disclosed systems, and kits for performing the disclosed methods. The disclosed systems, methods, and kits may be utilized to prepare a chemical product and to optimize conditions for preparing a chemical product. The disclosed systems, methods, and kits also may be utilized for combinatorial cell-free metabolism engineering.

16 Claims, 22 Drawing Sheets

(56) References Cited

OTHER PUBLICATIONS

Henrich, E. Hein C. Dotsch, V. & Bernhard, F. Membrane protein production in *Escherichia coli* cell-free lysates. FEBS Lett 589, 1713-1722, doi:10.1016/j.febslet.2015.04.045 (2015).

Hodgman, C. E & Jewett, M. C. Cell-free synthetic biology: thinking outside the cell. Metabolic engineering 14, 261-269, doi:10.1016/j.ymben.2011.09.002 (2012).

Hong, S. H. et al. Improving cell-free protein synthesis through genome engineering of *Escherichia coli* lacking release factor 1. Chembiochem 16, 844-853, doi:10.1002/cbic.201402708 (2015).

Inui M. et al. Expression of Clostridium acetobutylicum butanol synthetic genes in *Escherichia coli*. Appl Microbiol Biotechnol 77, 1305-1316, doi:10.1007/s00253-007-1257-5 (2008).

Jensen, M. K. & Keasling, J. D. Recent applications of synthetic biology tools for yeast metabolic engineering. FEMS Yeast Res, doi:10.1111/1567-1364.12185 (2014).

Jewett, M. C. & Swartz, J. R. Mimicking the *Escherichia coli* cytoplasmic environment activates long-lived and efficient cell-free protein synthesis. Biotechnol Bioeng 86, 19-26, doi:10.1002/bit.20026 (2004).

Jewett, M. C., Calhoun, K. A., Voloshin, A., Wuu, J. J. & Swartz, J. R. An integrated cell-free metabolic platform for protein production and synthetic biology. Mol Syst Biol 4, 220, doi:10.1038/msb.2008.57 (2008).

Jewett, M. C., Fritz, B. R., Timmerman, L. E. & Church, G. M. In vitro integration of ribosomal RNA synthesis, ribosome assembly, and translation. Mol Syst Biol 9, 678, doi:10.1038/msb.2013.31 (2013).

Kay, J. E & Jewett, M. C. Lysate of engineered *Escherichia coli* supports high-level conversion of glucose to 2,3-butanediol. Metabolic engineering 32, 133-142, doi:10.1016/j.ymben.2015.09.015 (2015).

Keasling, J. D. Manufacturing molecules through metabolic engineering. Science 330, 1355-1358, doi:10.1126/science.1193990 (2010).

Keasling, J. D. Synthetic biology and the development of tools for metabolic engineering. Metabolic engineering 14, 189-195, doi:10.1016/j.ymben.2012.01.004 (2012).

Kern, A., Tilley, E., Hunter, I. S., Legisa, M. & Glieder, A Engineering primary metabolic pathways of industrial micro-organisms. Journal of biotechnology 129, 6-29, doi:10.1016/jbiotec.2006.11.021 (2007).

Korman, T. P. et al. A synthetic biochemistry system for the in vitro production of isoprene from glycolysis intermediates. Protein Sci 23, 576-585, doi:10.1002/pro.2436 (2014).

Krutsakorn, B. et al. In vitro production of n-butanol from glucose. Metabolic engineering 20, 84-91, doi:10.1016/j.ymben.2013.09.006 (2013).

Kwok, R. Five hard truths for synthetic biology. Nature 463, 288-290, doi:10.1038/463288a (2010).

Lee, S. Y. & Kim, H. U. Systems strategies for developing industrial microbial strains. Nat Biotechnol 33, 1061-1072, doi:10.1038/nbt.3365 (2015).

Lee, J. W. et al. Systems metabolic engineering of microorganisms for natural and non-natural chemicals. Nature chemical biology 8, 536-546, doi:10.1038/nchembio.970 (2012).

Lutke-Eversloh, T. & Bahl, H. Metabolic engineering of Clostridium acetobutylicum: recent advances to improve butanol production. Current opinion in biotechnology 22, 634-647, doi:10.1016/j.copbio.2011.01.011 (2011).

Nielsen, D. R. et al. Engineering alternative butanol production platforms in heterologous bacteria. Metabolic engineering 11, 262-273, doi:10.1016/j.ymben.2009.05.003 (2009).

Nielsen, J. Metabolic engineering. Applied Microbiology and Biotechnology 55, 263-283, doi:10.1007/s002530000511 (2001).

Nielsen, J. et al. Engineering synergy in biotechnology. Nature chemical biology 10, 319-322, doi:10.1038/nchembio.1519 (2014).

Ninh, P. H., Honda, K., Sakai, T., Okano, K. & Ohtake, H. Assembly and multiple gene expression of thermophilic enzymes in *Escherichia coli* for in vitro metabolic engineering. Biotechnol Bioeng 112, 189-196, doi:10.1002/bit.25338 (2015).

Noireaux, V., Bar-Ziv, R. & Libchaber, A. Principles of cell-free genetic circuit assembly. Proc Natl Acad Sci U S A 100, 12672-12677, doi:10.1073/pnas.2135496100 (2003).

Record, M. T., Courtenay, E. S., Cayley, S. & Guttman, H. J. Biophysical compensation mechanisms buffering *E. coil* protein—nucleic acid interactions against changing environments. Trends in Biochemical Sciences 23, 190-194, doi:10.1016/50968-0004(98)01207-9 (1998).

Rollié, S., Mangold, M. & Sundmacher, K. Designing biological systems: Systems Engineering meets Synthetic Biology. Chemical Engineering Science 69, 1-29, doi:10.1016/j.ces.2011.10.068 (2012).

Shen, C. R. et al. Driving forces enable high-titer anaerobic 1-butanol synthesis in *Escherichia coli*. Applied and environmental microbiology 77, 2905-2915, doi:10.1128/AEM.03034-10 (2011).

Siegal-Gaskins, D., Tuza, Z. A., Kim, J., Noireaux, V. & Murray, R. M. Gene circuit performance characterization and resource usage in a cell-free "breadboard". ACS synthetic biology 3, 416-425, doi:10.1021/sb400203p (2014).

Smanski, M. J. et al. Functional optimization of gene clusters by combinatorial design and assembly. Nat Biotechnol 32, 1241-1249, doi:10.1038/nbt.3063 (2014).

Steen, E. J. et al. Metabolic engineering of *Saccharomyces cerevisiae* for the production of n-butanol. Microbial cell factories 7, 36, doi:10.1186/1475-2859-7-36 (2008).

Sun, Z. Z., Yeung, E., Hayes, C. A., Noireaux, V. & Murray, R. M. Linear DNA for rapid prototyping of synthetic biological circuits in an *Escherichia coli* based TX-IL cell-free system. ACS synthetic biology 3, 387-397, doi:10.1021/sb400131a (2014).

Swartz, J. R. Transforming biochemical engineering with cell-free biology. AIChE Journal 58, 5-13, doi:10.1002/aic.13701 (2012).

Voloshin, A. M. & Swartz, J. R. Efficient and scalable method for scaling up cell free protein synthesis in batch mode. Biotechnol Bioeng 91, 516-521, doi:10.1002/bit.20528 (2005).

Welch, P. & Scopes, R. K. Studies on cell-free metabolism: Ethanol production by a yeast glycolytic system reconstituted from purified enzymes. Journal of biotechnology 2, 257-273, doi:10.1016/0168-1656(85)90029-x (1985).

Yadav, V. G., De Mey, M., Giaw Lim, C., Kumaran Ajikumar, P. & Stephanopoulos, G. The future of metabolic engineering and synthetic biology: Towards a systematic practice. Metabolic engineering 14, 233-241, doi:10.1016/j.ymben.2012.02.001 (2012).

Yin, G. et al. Aglycosylated antibodies and antibody fragments produced in a scalable in vitro transcription-translation system. MAbs 4, 217-225, doi:10.4161/mabs.4.2.19202 (2012).

You, C. & Zhang, Y. H. Cell-free biosystems for biomanufacturing. Advances in biochemical engineering/biotechnology 131, 89-119, doi:10.1007/10_2012_159 (2013).

Zawada, J. F. et al. Microscale to manufacturing scale-up of cell-free cytokine production—a new approach for shortening protein production development timelines. Biotechnol Bioeng 108, 1570-1578, doi:10.1002/bit.23103 (2011).

Zemella, A., Thoring, L., Hoffmeister, C. & Kubick, S. Cell-Free Protein Synthesis: Pros and Cons of Prokaryotic and Eukaryotic Systems. Chembiochem 16, 2420-2431, doi:10.1002/cbic.201500340 (2015).

Zhang, Y. H. Production of biofuels and biochemicals by in vitro synthetic biosystems: Opportunities and challenges. Biotechnology advances 33, 1467-1483, doi:10.1016/j.biotechadv.2014.10.009 (2015).

Zhu F. et al. In vitro reconstitution of mevalonate pathway and targeted engineering of farnesene overproduction in *Escherichia coli*. Biotechnol Bioeng 111, 1396-1405, doi:10.1002/bit.25198 (2014).

Dudley, Quentin, et al., ACS Synth. Biol. 2016, 5, 1578-1588.
Dudley, Quentin, et al., Synthetic Biology, 2019, 4(1): ysz003.
Goering, Anthony, et al., ACS Synth. Biol. 2017, 6, 39-44.
Karim, Ashty, et al., Metabolic Engineering 36 (2016) 116-126.

CELL-FREE PROTEIN SYNTHESIS DRIVEN METABOLIC ENGINEERING FOR THE PRODUCTION OF 1-BUTANOL

CROSS-REFERENCE TO RELATED PATENT APPLICATIONS

The present application claims the benefit of priority under 35 U.S.C. § 119(e) to U.S. Provisional Patent Application No. 62/173,818, filed on Jun. 10, 2015, the content of which is incorporated herein by reference in its entirety.

STATEMENT REGARDING FEDERALLY SPONSORED RESEARCH OR DEVELOPMENT

This invention was made with government support under D14PC00005 awarded by the Defense Advanced Research Projects Agency (DARPA) (subcontract Agreement 10/24/14//D14PC00005/0001 Covitect Inc. STIR Award ST12B-003 to Northwestern University). The government has certain rights in the invention.

FIELD

The invention relates to cell-free systems for metabolic engineering, methods for cell-free metabolic engineering, and kits for preparing the systems, and kits for performing the methods. In particular, the invention relates to systems and methods for preparing a chemical product in cell-free conditions and to optimizing conditions for preparing a chemical product in cell-free conditions. The invention also relates to combinatorial cell-free metabolism engineering.

BACKGROUND

For decades scientists and engineers have turned to engineering biological systems for energy, medicine, materials, and more (Guo et al., 2015; Bornscheuer et al., 2012; Curran and Alper, 2012; Rollié et al., 2012). This has been an attractive, sustainable way to produce small molecules, especially when chemical synthesis is insufficient (Brown et al., 2014). The ability to harness organisms that naturally produce molecules of interest has expanded the chemical palate available (Demain, 2013; Harvey et al., 2015). Often when natural producers are not sufficient for production at the optimal quality or quantity, engineers turn to the power to manipulate biology (Kern, 2007). Our ability to introduce heterologous pathways into model microorganisms and metabolically engineer them to maximize small molecule production has led to large scale production of 1,3-propanediol, farnesene, and artemisinin with many more on their way to market (Hodgman and Jewett, 2012; Kwok, 2010). Efforts to make these molecules have resulted in success, but not without a great deal of challenges.

Bringing a biosynthetic molecule to market usually involves tireless efforts and countless hours of design-build-test (DBT) cycles (Kwok, 2010). The production of n-butanol is a prime example of these challenges. A series of *Clostridia* species are natural producers of this small molecule, and *Clostridia acetobutylicum* and *Clostridia bejinjernickii* are two of which are used in commercial butanol plants (Green, 2011). However, these species are difficult to engineer because of a biphasic metabolism, unknown regulation, and a limited number of species-specific engineering tools (Lütke-Eversloh and Bahl, 2011). Heterologous expression in model microorganisms like *E. coli* and *S. Cerevisiae* of Clostridial metabolism allows butanol production to be more easily engineered (Atsumi et al., 2008; Steen et al., 2008). Starting from a proof-of-concept, scientists have been able to increase titers dramatically by knocking out genes from genomes (Atsumi et al., 2008), increasing redox driving forces by introducing pathway independent enzymes (Shen et al., 2011), and identifying homologous enzymes with better activities (Bond-Watts et al., 2011). Years of iterative metabolic engineering led to these advances and many others in butanol biosynthesis, as is the same for most biosynthetic pathways.

Metabolic engineering is costly and time-consuming (Keasling, 2012). The constraints of cell membranes requiring a complete balancing of fluxes into and out of the cell makes it difficult to express biosynthetic pathways without taking into account the entire metabolic network. While there are many technologies that allow the engineer to better manipulate cells such as MFA, genome engineering, etc., the complexity of cells remains a limitation (Lee et al., 2012; Yadav et al., 2012). Furthermore, the tools we do have to regulate transcription, translation, and the genome require many DBT cycles increasing the time and effort needed to optimize the biosynthesis of interest (Boyle and Silver, 2014). Current DBT cycles are extraordinarily expensive. One estimate of the effort to develop new products has indicated current costs to be ~$10^8$-$10^{10}$ total \$*years to develop (Alicia Jackson, DARPA, personal communication). There is a clear need for speeding up and decreasing the cost of metabolic engineering DBT cycles. While techniques continue to be develop to engineer cells, in vitro systems show promise in speeding up DBT cycles because they bypass many in vivo limitations by having direct access to the cellular contents (Sun et al., 2013; You and Zhang, 2013; Siegal-Gaskins et al., 2014).

In vitro systems for biomolecular transformations have been established showing the potential for biomanufacturing and discovery (Dudley et. al, 2015). In particular, cell-free metabolic engineering (CFME) harnessing the power of crude *E. coli* extracts to express heterologous pathways was first spearheaded for the production 2,3-butanediol (Kay and Jewett, 2016). This work led to the development of an extract mixing approach to CFME whereby lysates containing selectively overexpressed heterologous enzymes are mixed together to construct a biosynthetic pathway that can be activated by the addition of simple substrates (Dudley and Jewett, in preparation). This previous work proved the utility of the extract mixing approach to CFME by carrying out a three-step from acetyl-CoA biosynthetic pathway. This approach has many advantages including only expressing one enzyme in each strain, not needing to fine-tune expression, and the lack of the cell membrane.

The approaches outlined above are, however, constrained by the need to express enzymes in cells. As a result, there still remains a need for systems and methods for cell-free metabolic engineering with in vitro expression of enzymes. Further, there still remains a need for systems and method for cell-free metabolic engineering amenable to combinatorial optimization to reduce the costs associated with DBT cycles.

SUMMARY

Disclosed are cell-free systems for metabolic engineering, methods for cell-free metabolic engineering, kits for preparing the systems, and kits for performing the methods. The disclosed systems, methods, and kits may be utilized to prepare a chemical product and to optimize conditions for preparing a chemical product. The disclosed systems, methods, and kits also may be utilized for combinatorial cell-free metabolism engineering.

The disclosed methods include methods for the enzymatic preparation of a chemical product in vitro. The methods may include one or more of the following steps: (a) providing a cell-free protein synthesis reaction mixture to a protein reaction vessel, the cell-free protein synthesis reaction mixture comprising a cellular extract (e.g., a cellular extract prepared from a host cell strain), a translation template, and cell-free protein synthesis reagents, (b) expressing the translation template in the protein reaction vessel to prepare an enzyme, (c) providing the enzyme, the cellular extract, and a metabolic reaction mixture to a metabolic reaction vessel, the metabolic reaction mixture comprising a feedstock, wherein the feedstock reacts in the presence of the enzyme to prepare the chemical product and wherein the cellular extract provides natural enzyme metabolism from the host strain. In certain embodiments, the natural enzyme metabolism from the host cell strain (i) provides energy; (ii) provides cofactor regeneration; (iii) provides a cellular extract enzyme; or (iv) any combination thereof. In certain embodiments, the translation template comprises two or more translation templates and wherein each of the two or more translation templates are expressed. In certain embodiments, the method further comprising providing a transcription template, a polymerase, ATP, GTP, CTP, and UTP to prepare the translation template, and in certain embodiments, the method further comprising providing salts.

In certain embodiments, the method further comprising (a1) providing a second cell-free synthesis reaction mixture to a second protein reaction vessel, the second cell-free protein synthesis reaction mixture comprising a second cellular extract (e.g., a cellular extract prepared from a host cell), a second translation template, and cell-free protein synthesis reagents, (b1) expressing the second translation template in the second protein reaction vessel to prepare a second enzyme, and (c1) providing the second enzyme to the metabolic reaction vessel, wherein the feedstock reacts in the presence of the enzyme and the second enzyme to prepare the chemical product. In certain embodiments, the method further comprising providing a second transcription template, a polymerase, ATP, GTP, CTP, and UTP to prepare the second translation template, and in certain embodiments, the method further comprising providing salts.

In certain embodiments, the protein reaction vessel and the metabolic reaction vessel are different. In certain embodiments, the protein reaction vessel and the metabolic reaction vessel are the same vessel. In certain embodiments, the protein reaction vessel and the second protein reaction vessel are different. In certain embodiments, the protein reaction vessel and the second protein reaction vessel are the same vessel.

In certain embodiments, between one and N cell-free protein synthesis reaction mixtures are used in the disclosed methods. For example, a combination of cell-free protein synthesis reaction mixtures may be used in the disclosed methods, where the combination comprises between 1 and N cell-free protein synthesis reaction mixtures In certain embodiments, the cellular extract (a) and/or the second cellular extract (a1) is a prokaryotic cellular extract. In further embodiments, the prokaryotic cellular extract is an *E. coli* cellular extract.

In certain embodiments, the cellular extract enzyme is a heterologous enzyme expressed in the host cell strain. In further embodiments, the cellular extract enzyme is overexpressed in the host cell to enrich a cellular extract prepared from the host cell with the cellular extract enzyme.

In certain embodiments, the cell-free protein synthesis reagents comprise a reaction buffer, amino acids, and a tRNA mixture. In further embodiments, the cell-free protein synthesis reagents further comprise a cofactor. In even further embodiments, the cell-free protein synthesis reagents comprise CoA, ATP, NAD, NADH, NADP, NADPH, FMN, SAM, potassium, magnesium, ammonium, glutamate, acetate, or any combination thereof.

In certain embodiments, the enzyme prepared in the disclosed methods, for example the enzyme in step (b) or the second enzyme i step (b1) is selected from the group consisting of AtoB, Hbd, Crt, Ter AdhE, and combinations thereof.

The disclosed methods may utilize a feedstock, for example, in step (c) or step (c1). The feedstock provides a carbon source, for example a C6, C5, C4, C3, C2, or C1 compound. In some embodiments, the feedstock comprises, consists essentially of, or consists of glucose or other carbohydrate sources. In other embodiments, the feedstock consists of cellulosic hydrolysates.

In certain embodiments, the metabolic reaction mixture further comprises a cofactor. In further embodiments, the metabolic reaction mixture comprises CoA, ATP, NAD, NADH, NADP, NADPH, FMN, potassium, magnesium, ammonium, glutamate, acetate, or any combinations thereof. In even further embodiments, the cofactor is coenzyme-A, NAD, ATP, or combinations thereof.

The disclosed methods also include methods for combinatorial cell-free metabolism engineering. The disclosed methods may include one or more of the following steps: (a) providing N solutions, (b) combining between one and $2^N$ combinations of the N solutions, (c) providing a cell-free protein synthesis reaction mixture, the cell-free protein synthesis reaction mixture comprising a cellular extract and a translation template, (d) combining the cell-free protein synthesis reaction mixture and at least one of the combinations of the N stock solutions in a cell-free protein synthesis reaction vessel, wherein the translation template is expressed to provide an enzyme; and (e) providing the enzyme and a feedstock to a metabolic reaction vessel, wherein the feedstock is capable of reacting in the presence of the enzyme to form a product. In certain embodiments, the feedstock reacts in the presence of the enzyme to form the product. In certain embodiments, the method further comprising measuring the amount of product formed. In certain embodiments, the cellular extract provides natural enzyme metabolism from the host strain. In certain embodiments, natural enzyme metabolism from the host strain (i) provides energy; (ii) provides cofactor regeneration; (iii) provides a cellular extract enzyme; or (iv) any combination thereof. In certain embodiments, the cellular extract enzyme is a heterologous enzyme expressed in the host. In certain embodiments, the cellular extract enzyme is overexpressed in the host to enrich the extract with the cellular extract enzyme. In certain embodiments, the method further comprising providing a transcription template and a polymerase to prepare the translation template. In certain embodiments, at least one of the solutions is a diluted solution of another of the solutions. In certain embodiments, at least one of the N solutions is selected from the group consisting of a nucleoside triphosphate solution, a tRNA solution, a salt solution, an amino acid solution, a cofactor solution, a protein helper factor solution and combinations thereof. In certain embodiments, the cell-free protein synthesis reaction vessel and the metabolic reaction vessel are the same vessel.

The disclosed methods also include methods for combinatorial cell-free metabolism engineering, which may include one or more of the following steps: (a) providing an enzyme, a cellular extract, a feedstock, and a metabolic reaction mixture, wherein the enzyme is prepared by cell-free protein synthesis, wherein metabolic reaction mixture comprises a member selected from the group consisting of a nucleoside triphosphate solution, a tRNA solution, a salt solution, an amino acid solution, a cofactor solution, a protein helper factor solution, and combinations thereof; wherein the feedstock is capable of reacting in the presence of the enzyme to form a product; wherein the cellular extract provides natural enzyme metabolism from the host strain. In certain embodiments, natural enzyme metabolism from the host strain (i) provides energy; (ii) provides cofactor regeneration; (iii) provides a cellular extract enzyme; or (iv) any combination thereof. In certain embodiments, the cellular extract enzyme is a heterologous enzyme expressed in the host. In certain embodiments, the cellular extract enzyme is overexpressed in the host to enrich the extract with the cellular extract enzyme.

Also disclosed are kits for preparing the disclosed systems and kits for performing the disclosed methods. The disclosed kits may include one or more of the following components: (a) a solution, the solution comprising a nucleoside triphosphate solution, a tRNA solution, a salt solution, an amino acid solution, a cofactor solution, a protein helper factor solution or combinations thereof; and (b) a cell-free protein synthesis reaction mixture, the cell-free protein synthesis reaction mixture comprising a cellular extract and a translation template. In certain embodiments, the kit further comprises a feedstock. In certain embodiments, the cellular extract provides natural enzyme metabolism from the host strain. In certain embodiments, natural enzyme metabolism from the host strain (i) provides energy; (ii) provides cofactor regeneration; (iii) provides a cellular extract enzyme; or (iv) any combination thereof. In certain embodiments, the cellular extract enzyme is a heterologous enzyme expressed in the host. In certain embodiments, the cellular extract enzyme is overexpressed in the host to enrich the extract with the cellular extract enzyme.

BRIEF DESCRIPTION OF THE DRAWINGS

Non-limiting embodiments of the presently disclosed cell-free systems, methods, and kits may be described by way of example with reference to the accompanying figures, which are schematic and may not be intended to be drawn to scale. In the figures, each identical or nearly identical component illustrated may be represented by a single numeral. For purposes of clarity, not every component may be labeled in every figure, nor is every component of each embodiment of the invention shown where illustration is not necessary to allow those of ordinary skill in the art to understand the invention.

Glucose, CoA, and NAD$^+$ were added to activate the n-butanol pathway and CFME reactions were incubated for 24 h at 30° C. (c) n-butanol production activated by CFPS of enzymes in combinations: (1) AtoB (EC); (2) AtoB (EC) and Hbd2 (CB); (3) AtoB (EC), Hbd2 (CB), and Crt1 (CA); (4) AtoB (EC), Hbd2 (CB), Crt1 (CA), and Ter1 (TD); and (5) AtoB (EC), Hbd2 (CB), Crt1 (CA), Ter1 (TD), and AdhE1 (CA). The CFPS reactions were run at 30° C. for 3 hrs. Glucose, CoA, and NAD$^+$ were added to activate the n-butanol pathway and reactions were incubated for 24 h at 30° C. (d) A plasmid ratio optimization of pJL1-adhE1 vs. all other pJL1 constructs along with a test of three concentrations of T7 polymerase. For each, CFPS was run at 30° C. for 3 h. Glucose, CoA, and NAD$^+$ were added to activate the n-butanol pathway and reactions were incubated for 24 h at 30° C. All error bars represent standard deviations with n≥3 independent reactions.

Figure 6:
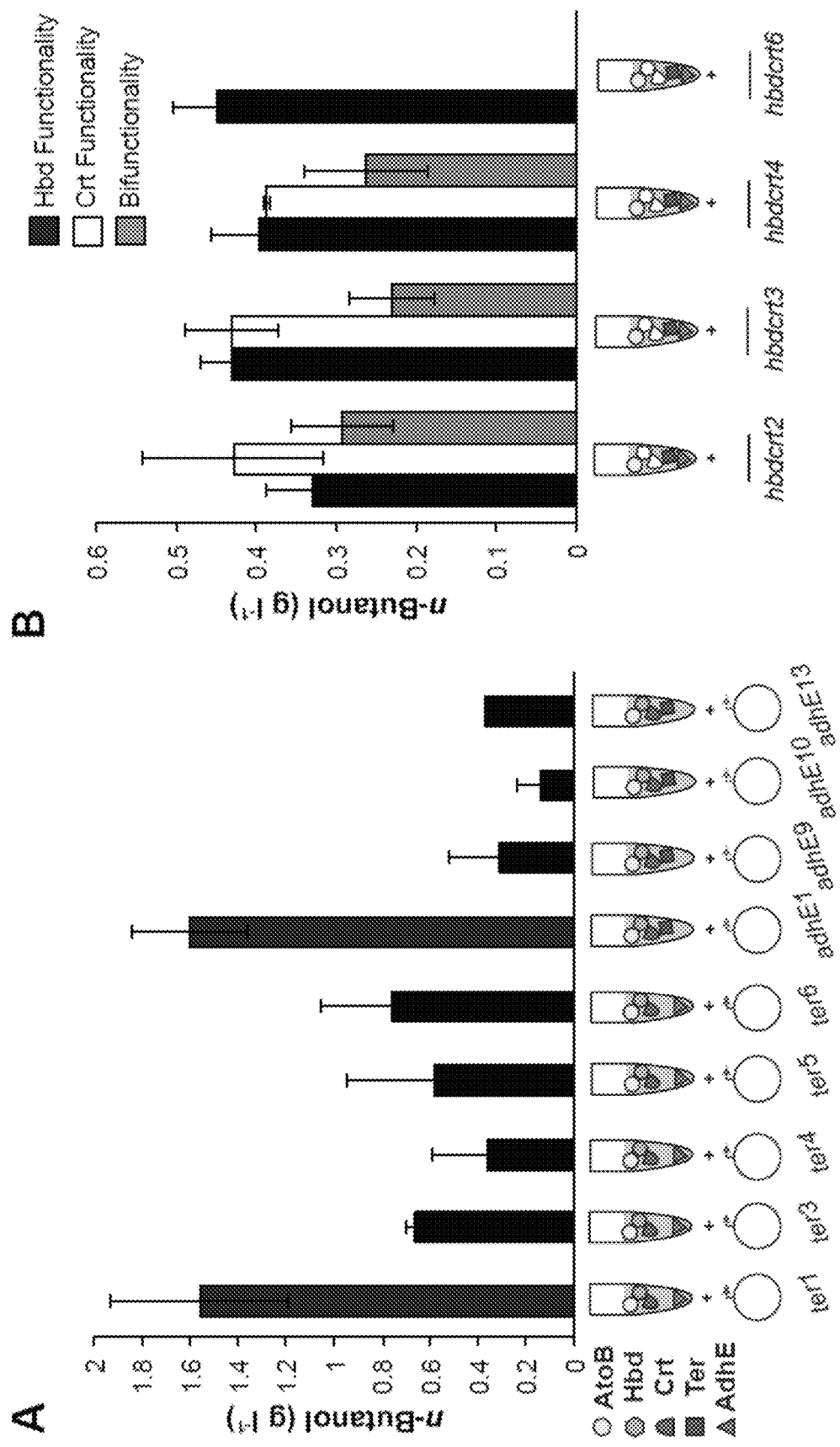

FIG. 6. Using CFPS-ME to rapidly screen pathway enzymes. (A) n-butanol production activated by CFPS of unique Ter homologs and AdhE homologs from pJL1 constructs: Ter3 (*Fibrobacter succinogenes*, FS), Ter4 (*Flavobacterium johnsoniae*, FJ), Ter5 (*Spirochaeta bajacaliforniensis*, SB), Ter6 (*Cytophaga hutchinsonii*, CH), AdhE9 (*Thermosynechococcus* sp. NK55a, TN), AdhE10 (*Providencia burhodogranariea*, PB), and AdhE13 (*Serratia marcescens*, SM). Ter homologs were expressed in crude lysate mixtures containing AtoB (EC), Hbd2 (CB), Crt1 (CA), and AdhE1 (CA) overexpressed, and AdhE homologs were expressed in lysates containing AtoB (EC), Hbd2 (CB), Crt1 (CA), and Ter1 (TD) overexpressed. (B) n-Butanol production activated by CFPS putative bifunctional enzymes for Hbd and Crt activity: Hbdcrt2 (*Aeropyrum camini*, AC), Hbdcrt3 (*Pyrobaculum aerophilum*, PA), Hbdcrt4 (*Sulfolobus islandicus*, SI), and Hbdcrt6 (*Sulfolobus acidocaldarius*, SA). CFPS reactions were performed from linear DNA in crude lysate mixtures containing: (1) AtoB (EC), Ter1 (TD), and AdhE1 (CA) overexpressed to test biofunctionality, (2), AtoB (EC), Crt1 (CA), Ter1 (TD), and AdhE1 (CA) overexpressed to test Hbd functionality alone, and (3) AtoB (EC), Hbd2 (CB), Ter1 (TD), and AdhE1 (CA) overexpressed to test Crt functionality alone. For each, CFPS was run at 30° C. for 3 h. Glucose, CoA, and NAD$^+$ were added to activate the n-butanol pathway and reactions were incubated for 24 h at 30° C. All error bars represent standard deviations with n≥3 independent reactions.

Figure 7:
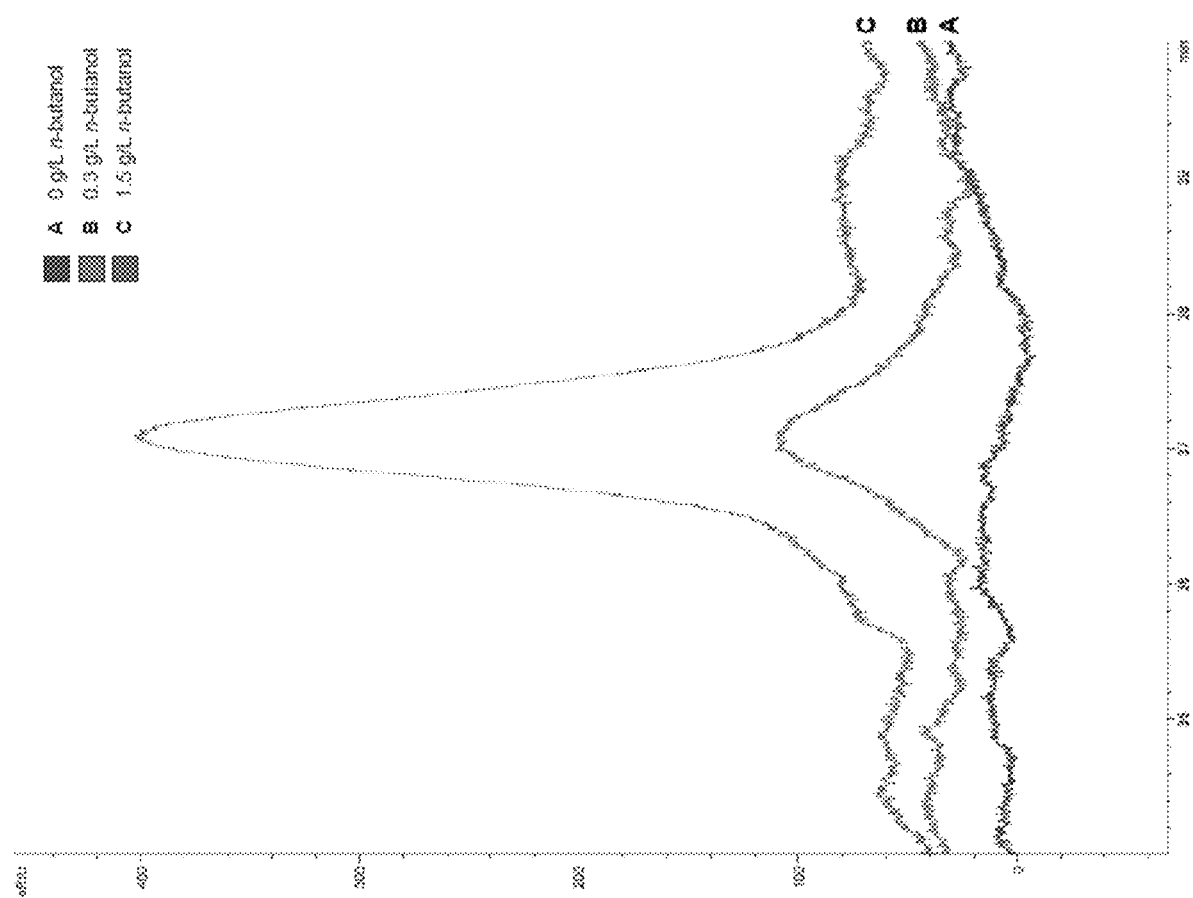

FIG. 7. Example Chromatograms for n-butanol quantification. Three chromatogram n-butanol peaks are overlaid with retention time on the x-axis and relative intensity units of the y-axis. Peak A represents an example cell-free reaction with no n-butanol produced from the reaction. Peak B is a cell-free reaction with ~0.3 g/L of n-butanol produced. Peak C is a cell-free reaction with ~1.5 g/L of n-butanol produced.

Figure 8:
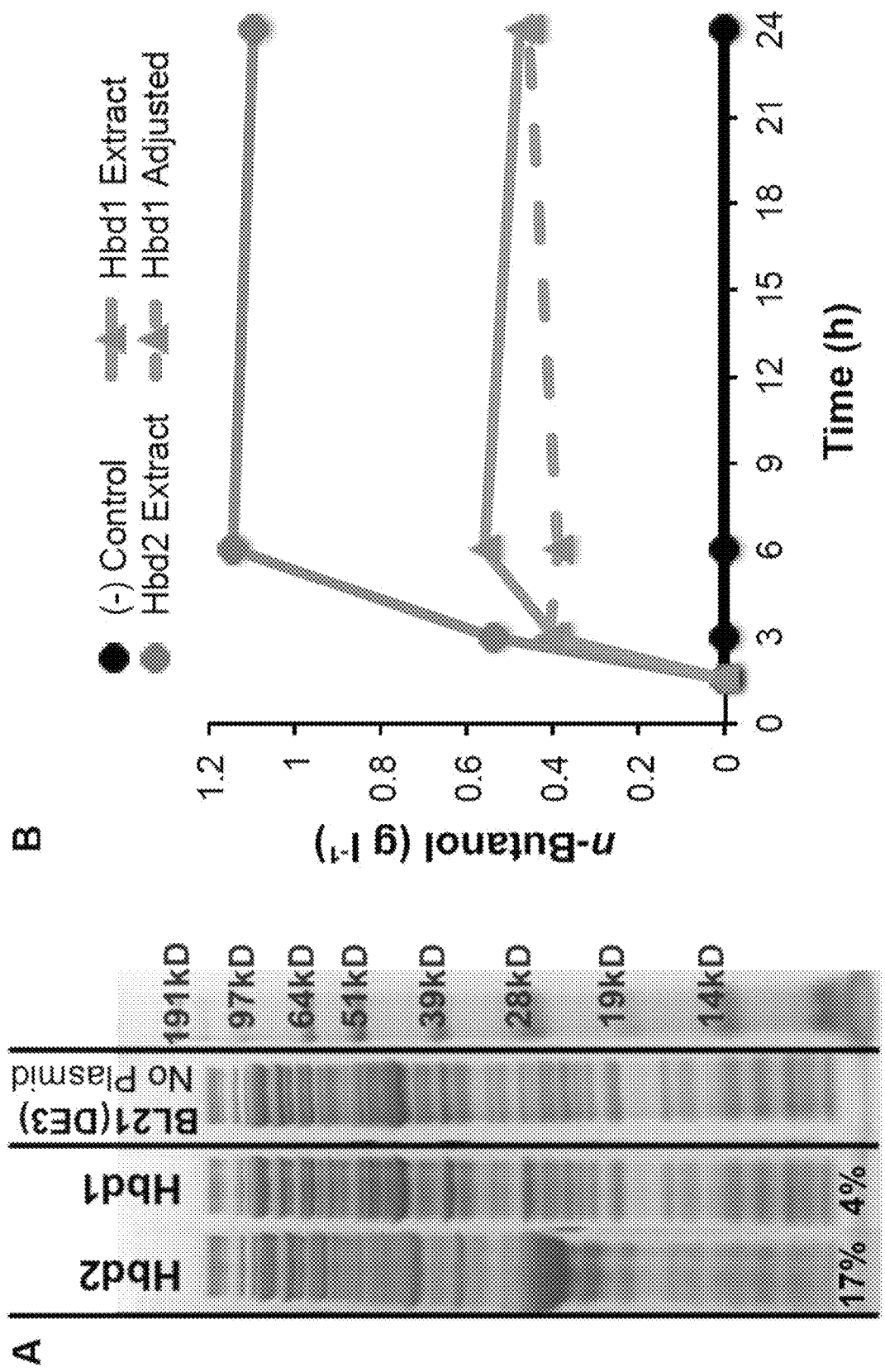

FIG. 8. Adjusting extracts for relative concentrations of selectively overexpressed Hbd1 and Hbd2 does not affect overall n-butanol production by CFME. (A) BL21(DE3) extract containing no overexpressed proteins, overexpressed Hbd1 extract, and overexpressed Hbd2 extract were each separated by SDS-PAGE and stained with Coomassie blue. Using densitometry with ImageJ software, each lane was analyzed for band density to determine approximate, relative amounts of overexpressed protein. Hbd1 extract contained ~4% Hbd1 protein, and Hbd2 extract contained ~17% Hbd2 protein. (B) Each Hbd extract was mixed with extracts containing the other pathway enzymes (AtoB, Crt, Ter, and AdhE) and CFME reactions were run for 24 h (n=1) to make n-butanol. The cases include Hbd2 extract, Hbd1 extract, and Hbd1 extract adjusted to contain approximately the same amount of overexpressed Hbd protein as the Hbd2 extract. Total extract concentration was kept constant at 10 μg ml$^{-1}$ using a BL21(DE3) extract containing no heterologously expressed proteins to adjust the Hbd extracts. The observed discrepancies in 'Hbd1 Extract' and 'Hbd1 Adjusted' are likely an artifact of sample size.

Figure 9:
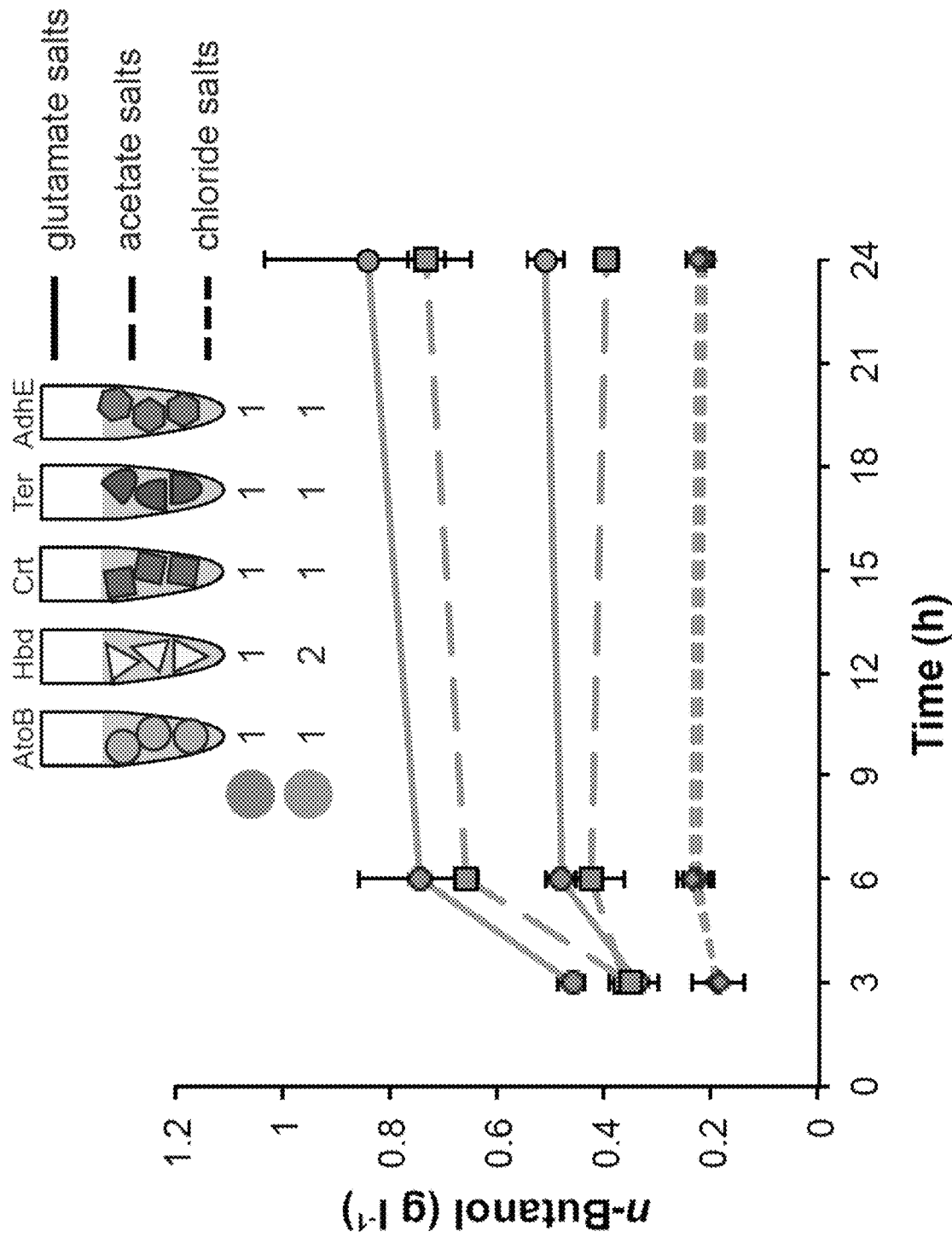

FIG. 9. Inorganic glutamate salt solutions perform the best in CFME reactions. Two different sets of 5 crude lysates mixed together containing selectively overexpressed enzymes with AtoB, Hbd, Crt, Ter, and AdhE activities were used to produce n-butanol from glucose. Blue is the original set of extracts (containing Hbd1) and orange is the best enzyme set (containing Hbd2). Lysate mixes were combined with glutamate salts (Mg$^+$, NH$_4^+$, K$^+$) (solid line), acetate salts (long dashed line), or chloride salts (short dashed line). To activate metabolism and start CFME reactions phosphates (K$_2$HPO$_4$), buffer (Bis Tris), and cofactors (ATP, CoA, NAD$^+$) were added and incubated for 24 h at 37° C. All error bars represent 1 s.d. with n≥3.

Figure 10:
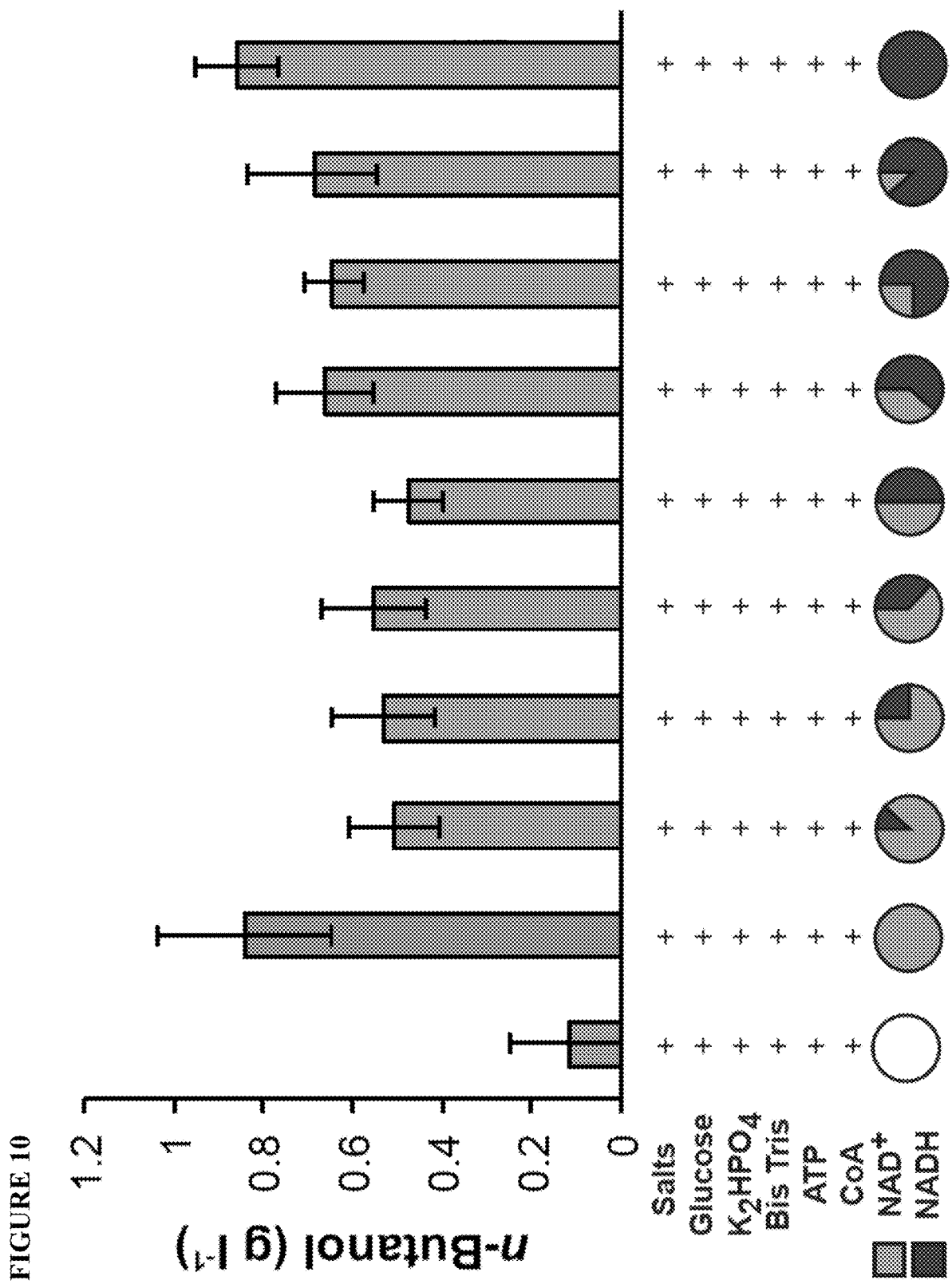

FIG. 10. Comparing initial NAD$^+$ and NADH ratios show relatively little effect on n-butanol production in CFME. Reactions for n-butanol production from glucose using the best set of crude lysates mixed together containing selectively overexpressed enzymes with AtoB, Hbd, Crt, Ter, and AdhE activities (determined as best by previous experiments) were run for 24 h and incubated at 37° C. Extract mixes were combined with glutamate salts (Mg$^+$, NH$_4^+$, K$^+$), phosphates (K$_2$HPO$_4$), buffer (Bis Tris), and cofactors (ATP, CoA, NAD$^+$, NADH) to initiate CFME reactions. In the key, plus signs (+) indicate the addition of each individual components at levels described in the methods section. The divisions in the circular graphics accompanying each bar with blue being NAD$^+$ and black being NADH indicate ratios of NAD$^+$ to NADH. The total NAD(H) concentration is 0.5 mM. All error bars represent 1 s.d. with n≥3.

Figure 11:
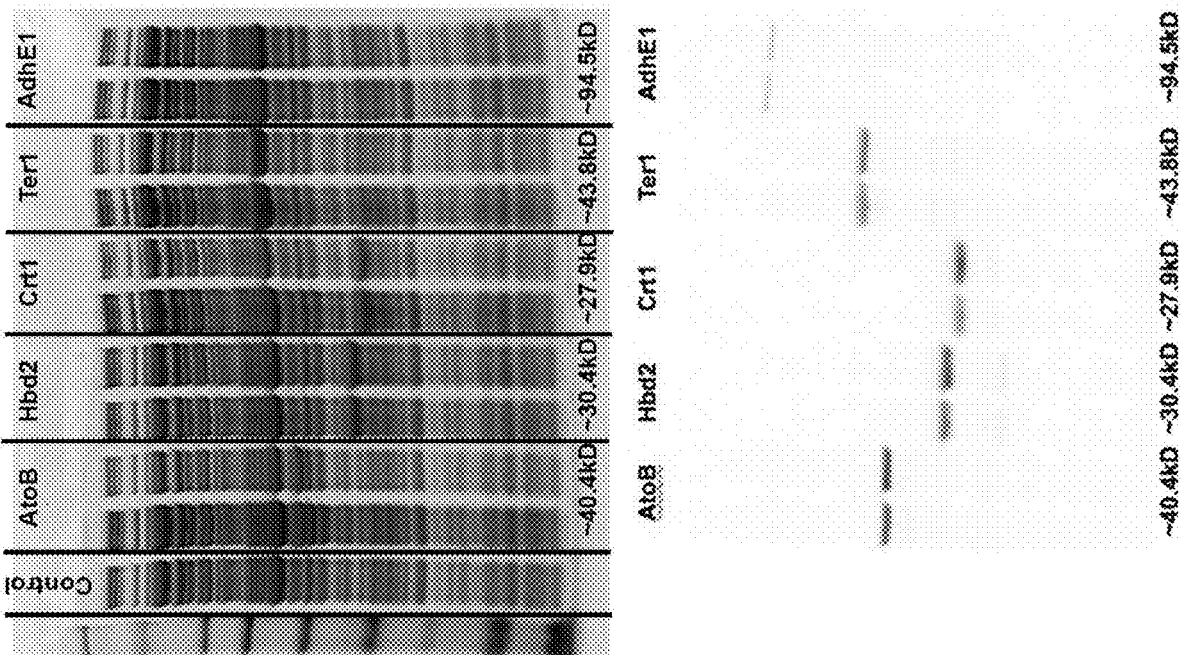

FIG. 11. SDS-PAGE and autoradiogram for CFPS of each individual enzyme show full-length protein formation. (A) SDS-PAGE was run with two replicates of each CFPS reaction performed at standard conditions listed in the methods section and for 3 h at 30° C. producing $^{14}$C-Leu incorporated protein corresponding to each enzyme in the n-butanol pathway. Molecular weights are listed at the bottom of the lanes. (B) An autoradiogram of the same gel showing that each enzyme is expressed in vitro as full-length proteins.

Figure 12:
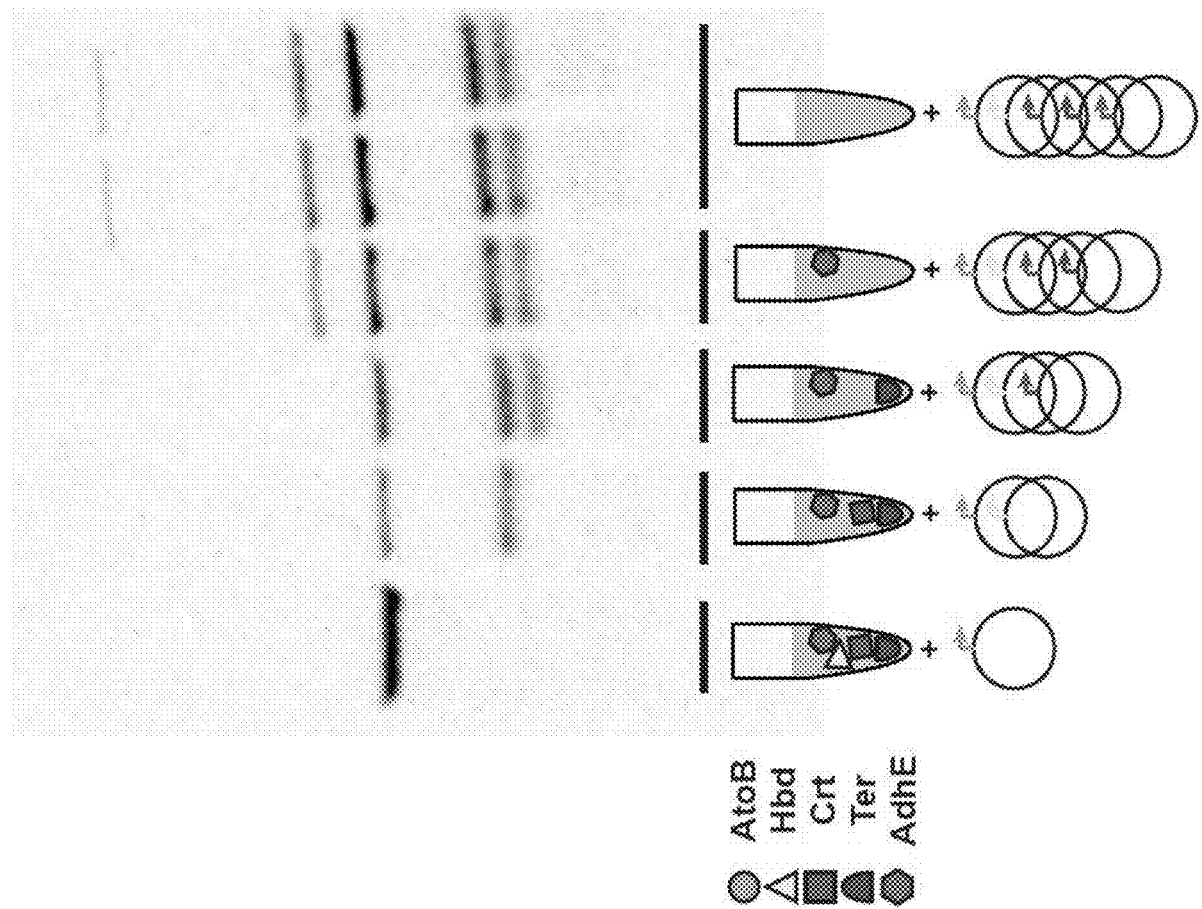

FIG. 12. Protein SDS-PAGE gel and autoradiogram for CFPS of multiple enzymes produced full length product of each protein. SDS-PAGE was run with CFPS reactions containing one, two, three, four, and five DNA plasmids, building up the pathway. Reactions were each run at standard conditions listed in the methods section and for 3 h at 30° C. producing $^{14}$C-Leu incorporated protein corresponding to each enzyme in the n-butanol pathway.

Figure 13:
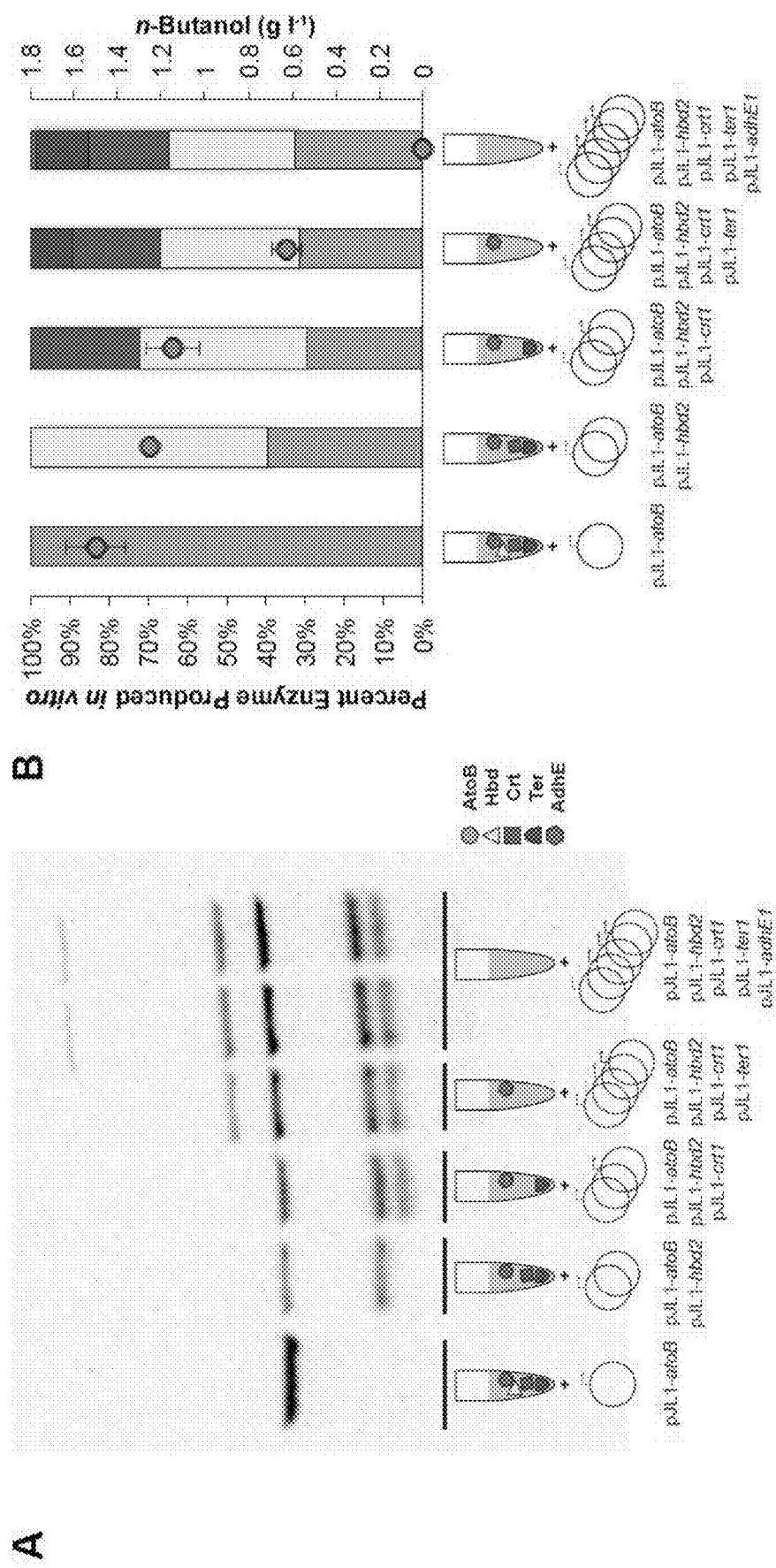

FIG. 13. Quantification of individual enzymes in multiple protein CFPS reactions from autoradiogram indicates a lower yield of downstream pathway enzymes. (A) BL21 (DE3) extract containing overexpressed proteins indicated in the key, different DNA plasmid compositions, and standard CFPS reagents identified in the methods section were incubated at 30° C. for 3 h. Each sample was separated by SDS-PAGE and stained with Coomassie blue. The gel was exposed to autoradiogram showing full-length product of each enzyme resulting from the DNA combinations. (B) Using densitometry with ImageJ software, each lane from the gel in panel A was analyzed for band density to determine approximate, relative amounts of each pathway enzyme produced by CFPS. The bars represent the percent of each enzyme produced in vitro. After CFPS for 3 h at 30° C., each reaction was supplemented with glucose, NAD+, and CoA and incubated at 30° C. for an additional 24 h to measure n-butanol production from each mix. Orange circles indicate n-butanol titers with error bars representing 1 s.d. with n≥3.

Figure 14:
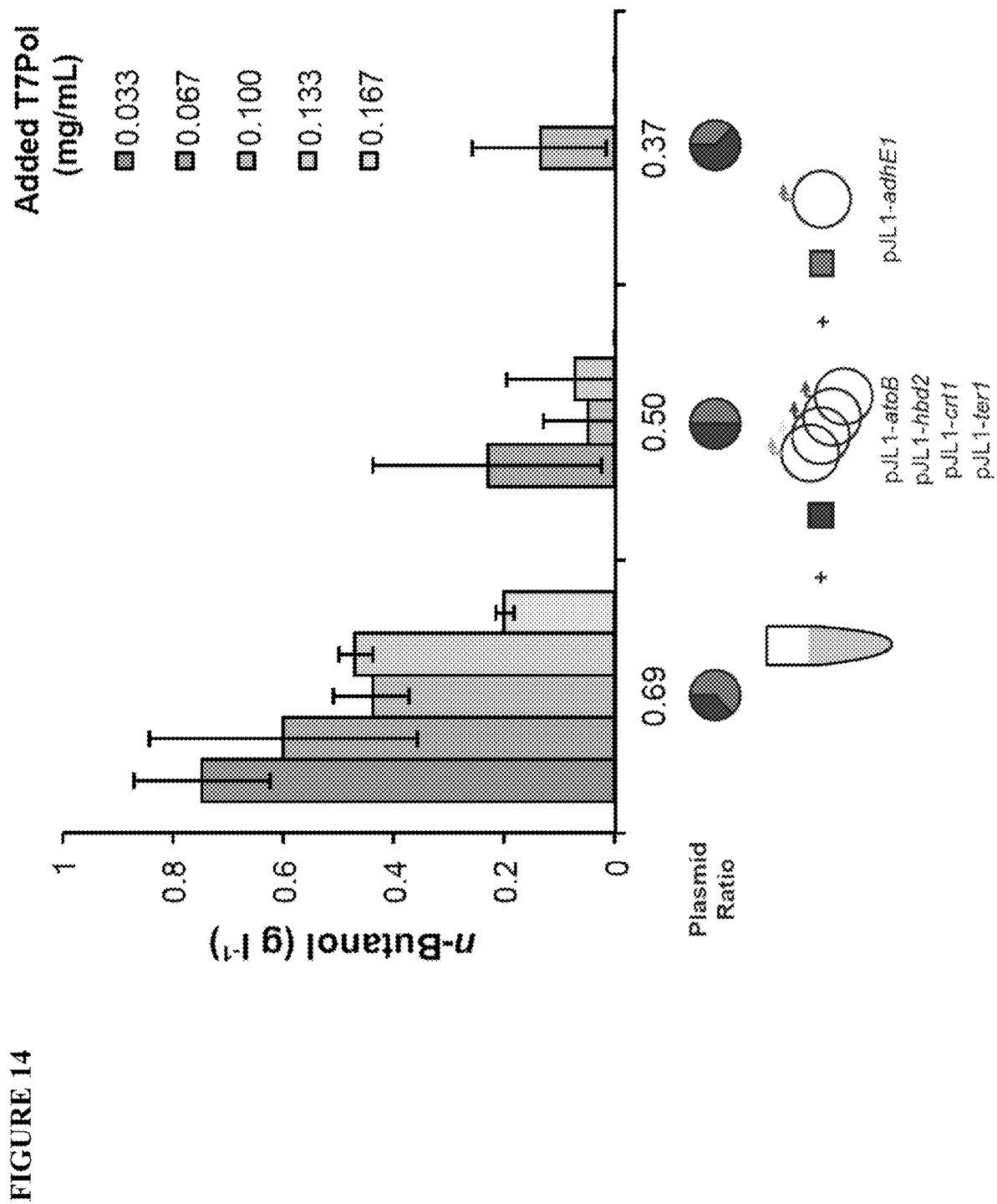

FIG. 14. Plasmid optimization for CFPS-ME of all pathway enzymes in vitro shows the ability to produce n-butanol. CFPS reactions were run in BL21(DE3) extract containing no overexpressed proteins. DNA plasmids encoding each heterologous enzyme were added in equal ratios with pJL1-adhE1 modulated as per the divisions in the circular graphics in the figure key. In the key, black represents equal amounts of plasmids encoding AtoB, Hbd, Crt, and Ter, and red represents the amount of pJL1-adhE1. CFPS reagents were added and incubated at 30° C. for 3 h. Glucose, NAD+, and CoA were added, and samples were further incubated at 30° C. for 24 h. n-Butanol production is measured and differs with varied concentrations of added T7 polymerase. All error bars represent 1 s.d. with n≥3.

Figure 15:
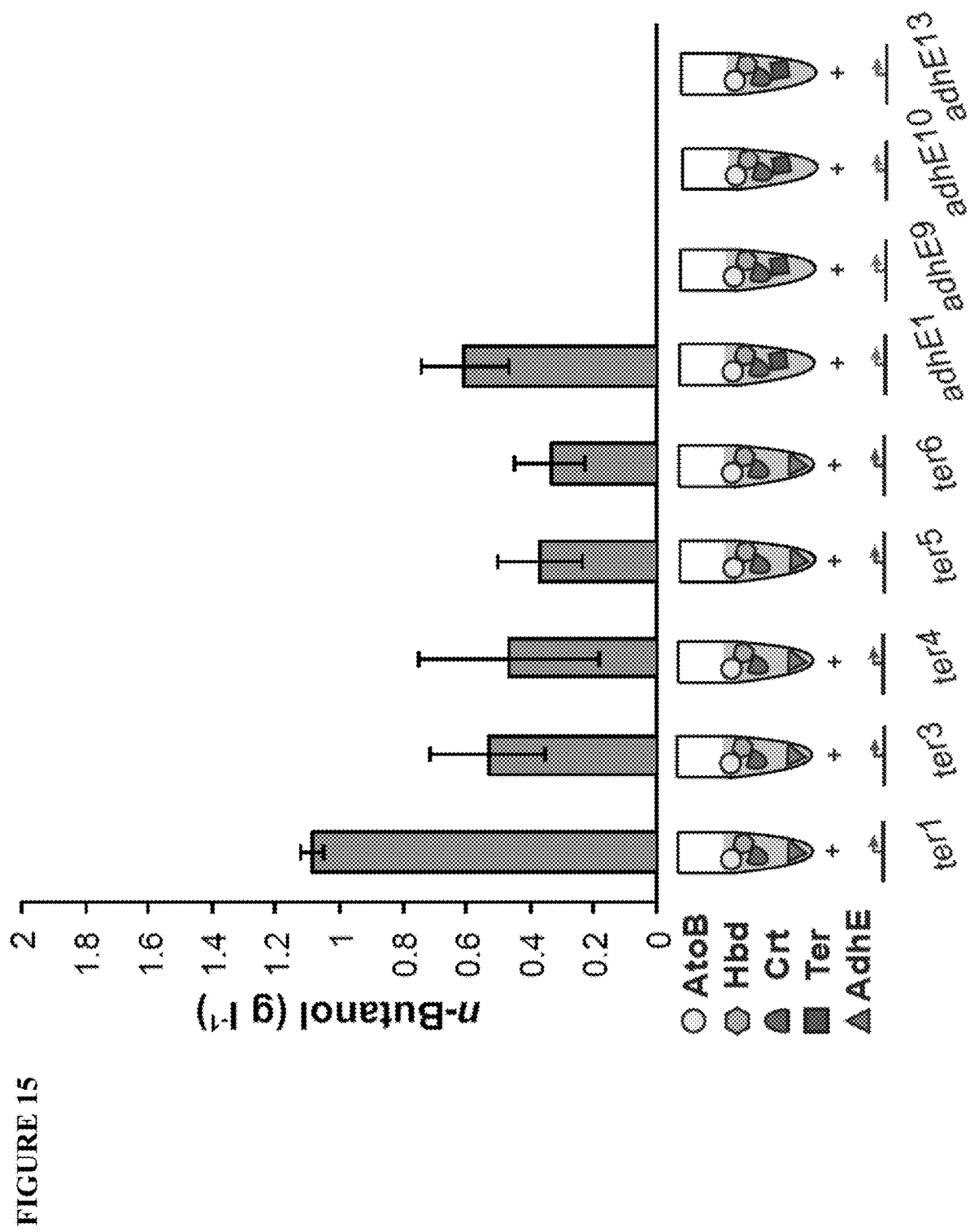

FIG. 15. Using CFPS-ME to rapidly screen pathway enzymes from linear DNA templates. Linear DNA of each enzyme variants were created with the regulatory elements from pJL1 and with a randomized ~20 bp on each end and used as DNA template in each CFPS reaction. CFPS of each enzyme variant (Ter and AdhE) was used to activate n-butanol production in crude lysate mixtures containing AtoB (EC), Hbd2 (CB), Crt1 (CA), and AdhE1 (CA) overexpressed or AtoB (EC), Hbd2 (CB), Crt1 (CA), and Ter1 (TD) overexpressed, respectively. All error bars represent 1 s.d. with n≥3.

Figure 16:
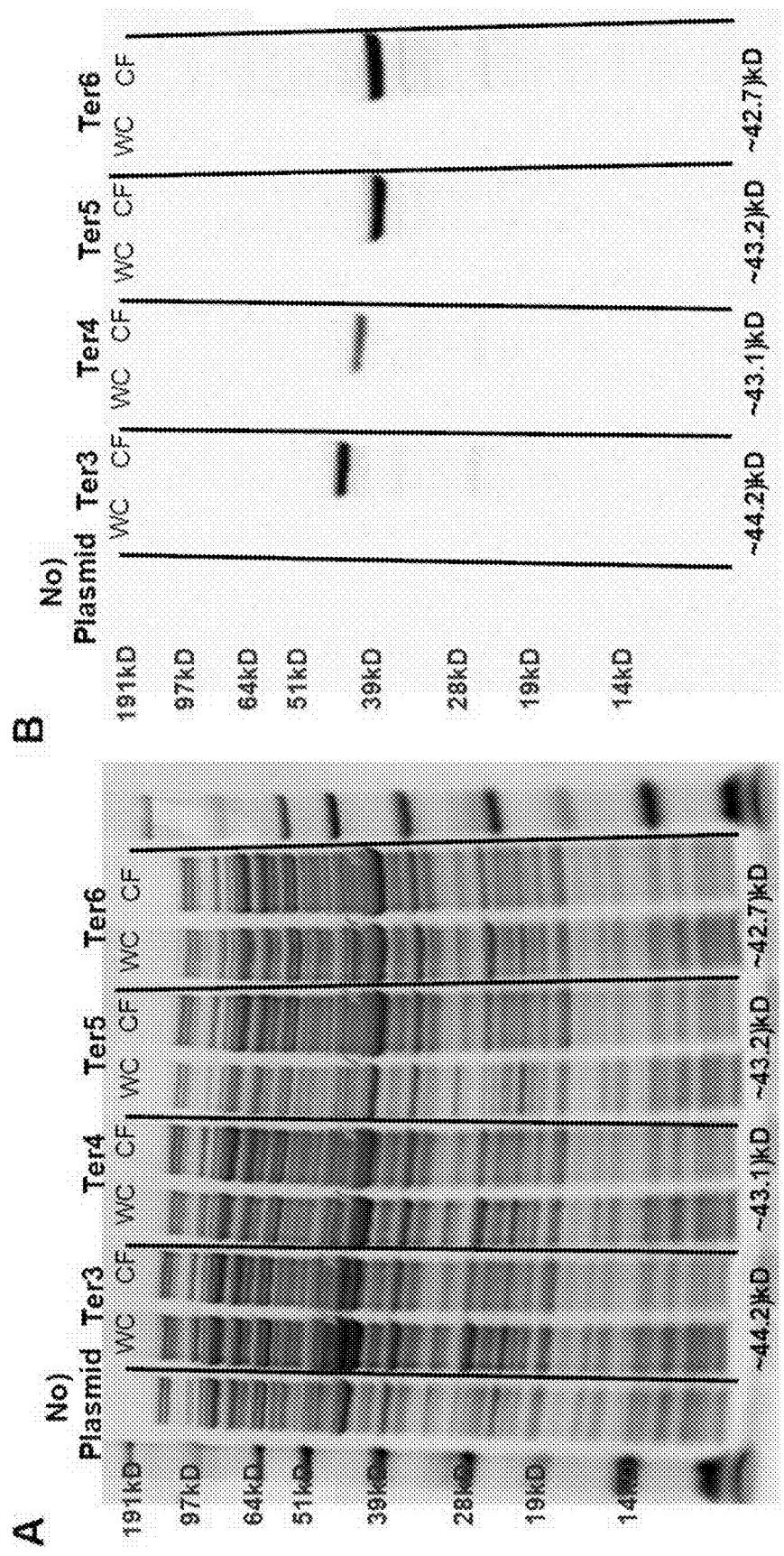

FIG. 16. Expression of Ter homologs in cells versus cell-free. SDS-PAGE was run on samples expressing the Ter homologs screened in FIG. 6. The first lane is the SeeBlue Plus2 Pre-stained standard. The second lane is a no plasmid (negative) control in BL21(DE3). For each homolog, the WC lane is a whole cell sample taken 4 hours after induction, and the CF lane is a cell-free protein synthesis sample taken after 3 hours of expression. (A) Coomassie-stained gel. While expression of Ter5 in the WC lane in an unoptimized (generic RBS) single attempt is unobservable, the other Ter enzymes are expressed, which confirms that our approach holds promise for identifying good enzymes that can be expressed in cells. (B) An autoradiogram of the same gel showing that each enzyme is expressed in vitro. As the in vivo expression did not incorporate radioactive leucine, bands are not expected in the WC lanes in panel B.

Figure 17:
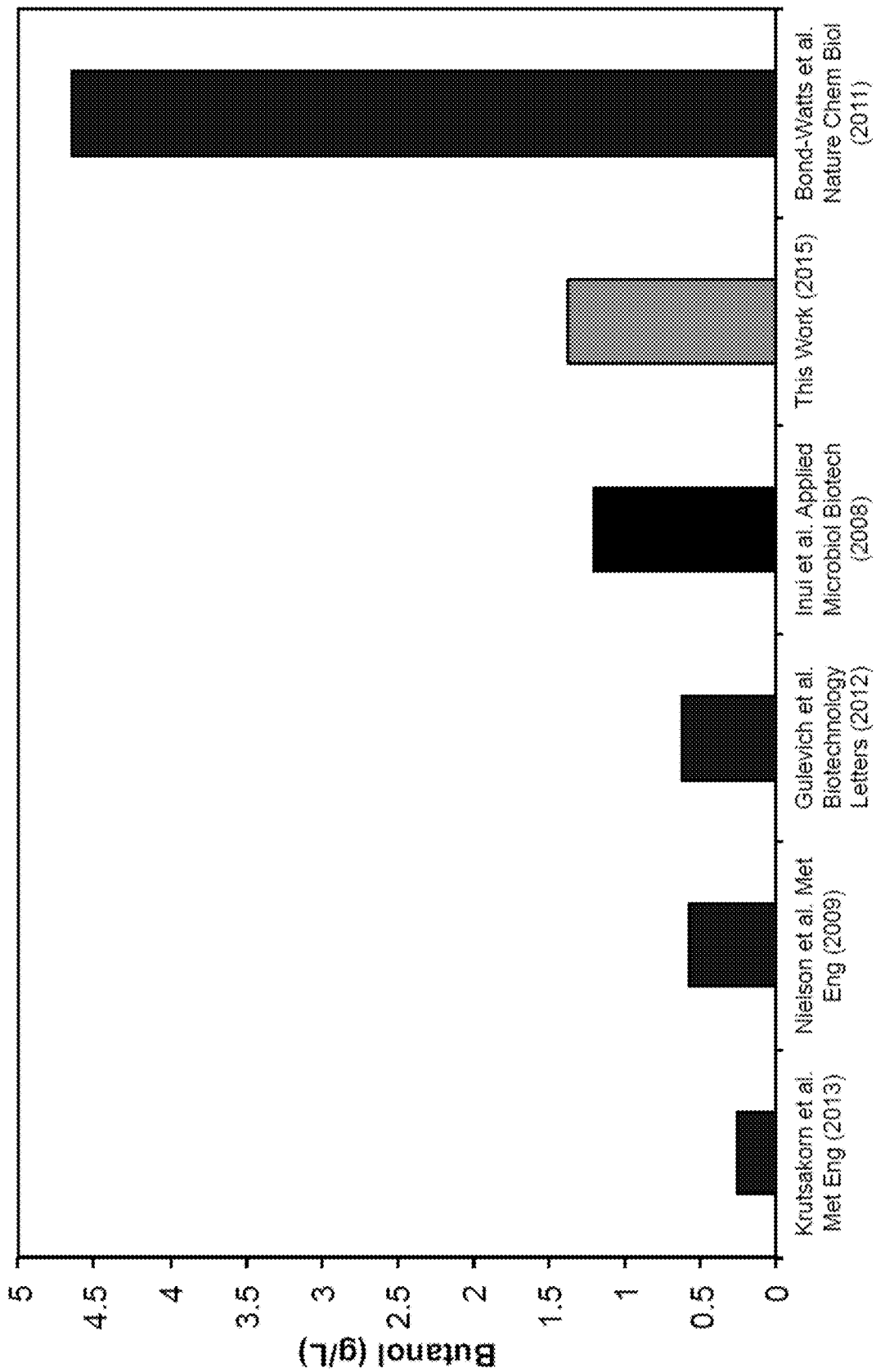

FIG. 17. Comparison of n-butanol production in genomically unmodified hosts. Final titers (g/L) of n-butanol are reported from recent studies using genomically unmodified host strains. The Krustakorn et al. 2013 study is the only other in vitro n-butanol production system (uses purified enzymes). The highest titer from this study is reported in orange.

Figure 18:
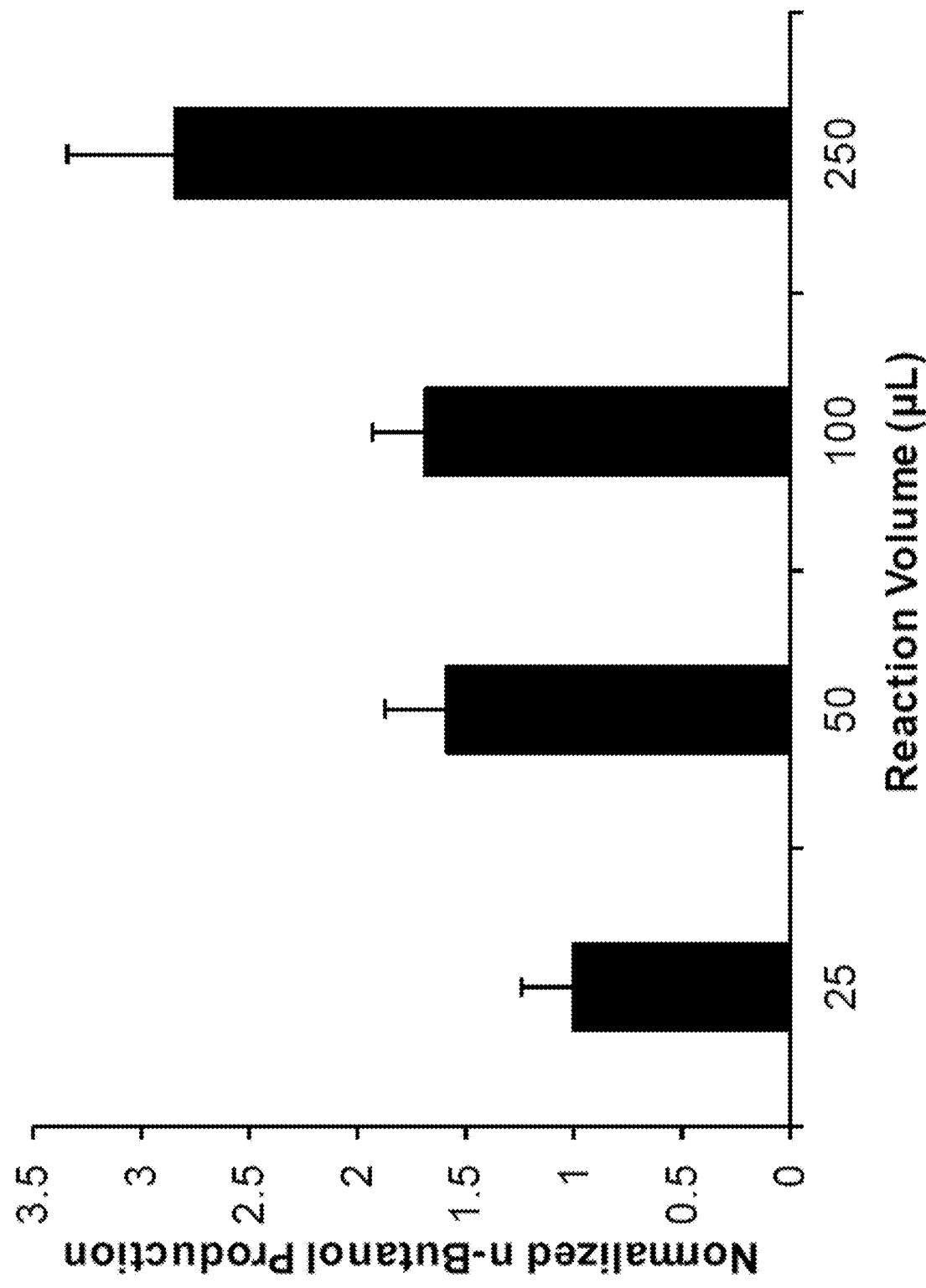

FIG. 18. Scale-up of CFPS-ME reactions. CFPS reactions were run in BL21(DE3) extract containing no overexpressed proteins in 1.5 mL Eppendorf tubes. DNA plasmids encoding each heterologous enzyme were added in equal ratios with pJL1-adhE1 representing 70% of the total DNA. CFPS reagents were added and incubated at 30° C. for 3 h. Glucose, NAD+, and CoA were added, and samples were further incubated at 30° C. for 24 h. The total reaction volumes are listed on the x-axis with the data normalized to 254, reactions. Increasing the reaction volume improved overall butanol yields. All error bars represent 1 s.d. with n≥3.

Figure 19:
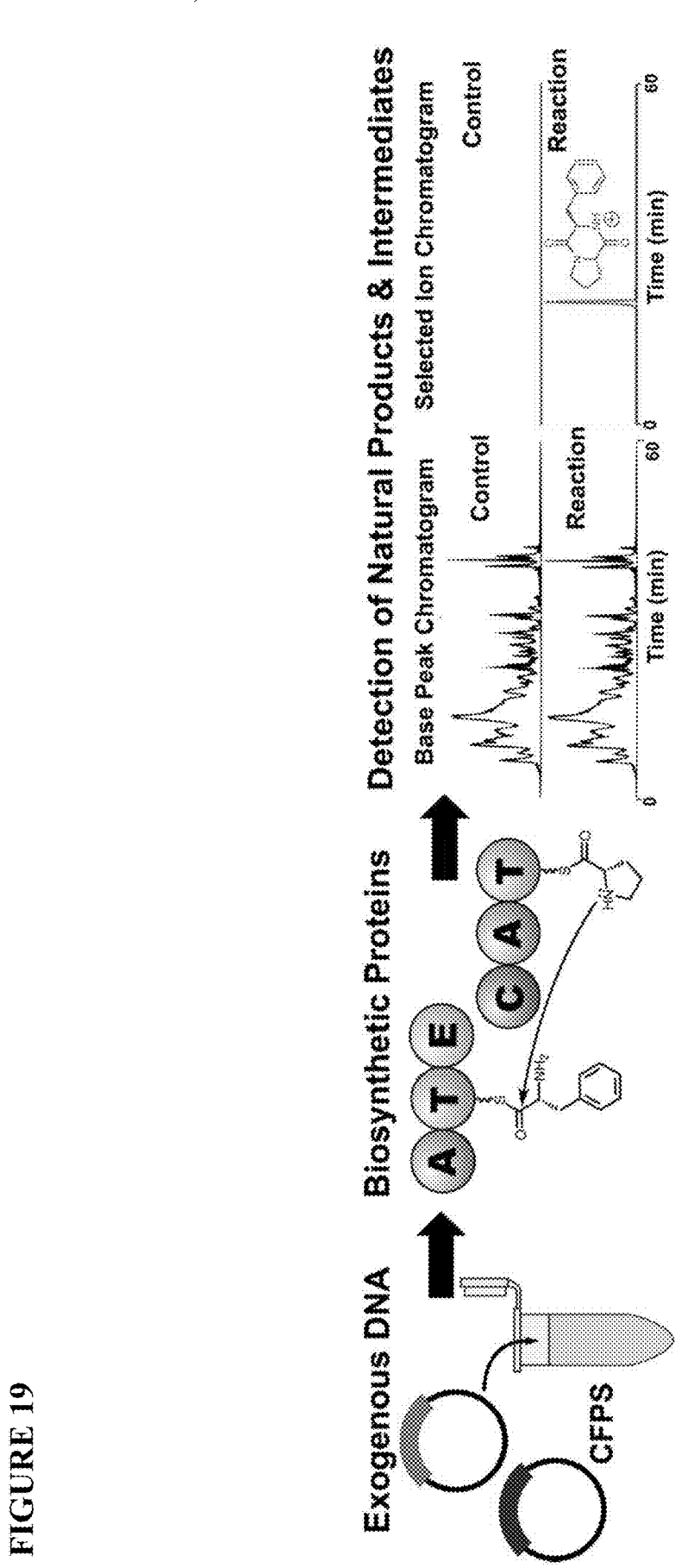

FIG. 19. Overview of a system for cell-free production of natural products via nonribosomal peptide biosynthesis by using cell-free protein synthesis driven metabolic engineering. From left to right, exogenous DNA is used as the input information for the production of biosynthetic enzymes. In the center, nonribosomal peptide synthetase proteins function in concert to select substrates and catalyze the formation of peptide bonds, ultimately resulting in the production of a 2,5-diketopiperazine. Right panel, detection of a D-Phe-L-Pro diketopiperazine (DKP) natural product by LC-MS as the result of in situ production of biosynthesis proteins.

Figure 20:
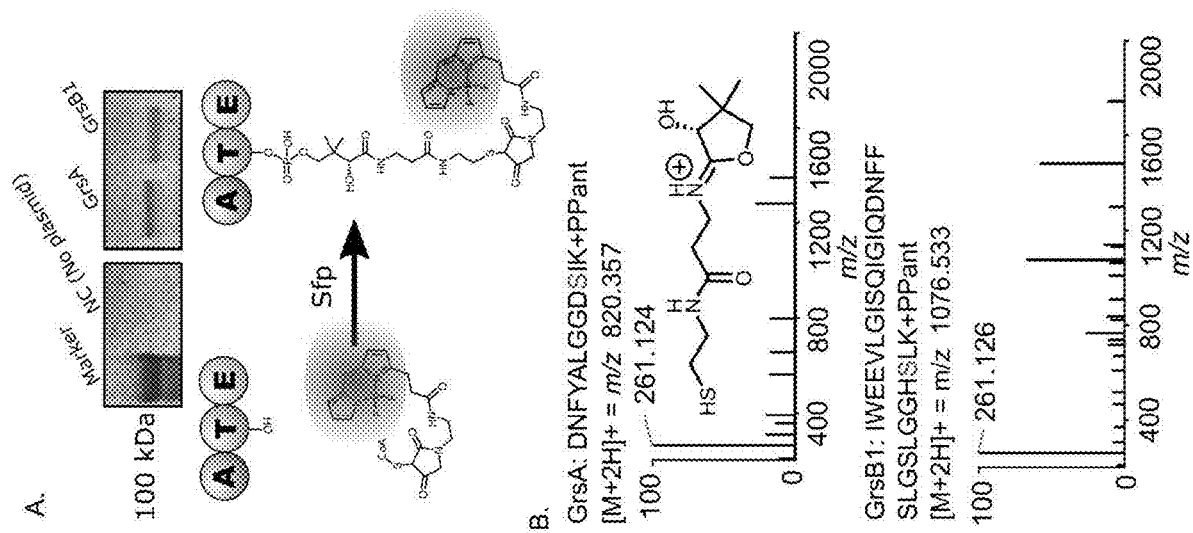

FIG. 20. Experiments showing that GrsA and GrsB1 are present in their active (holo) forms. Panel A shows the fluorescent labeling of GrsA and GrsB1 on the thiolation domain active sites with a conjugated BODIPY-CoA fluorophore. Panel B top shows the $MS^2$ spectrum resulting from the fragmentation of a precursor peptide containing the GrsA phosphopantetheine modification. Panel B bottom shows the $MS^2$ spectrum for the corresponding GrsB1 T-domain peptide, indicating the mass of the observed pantetheine-derived ion.

Figure 21:
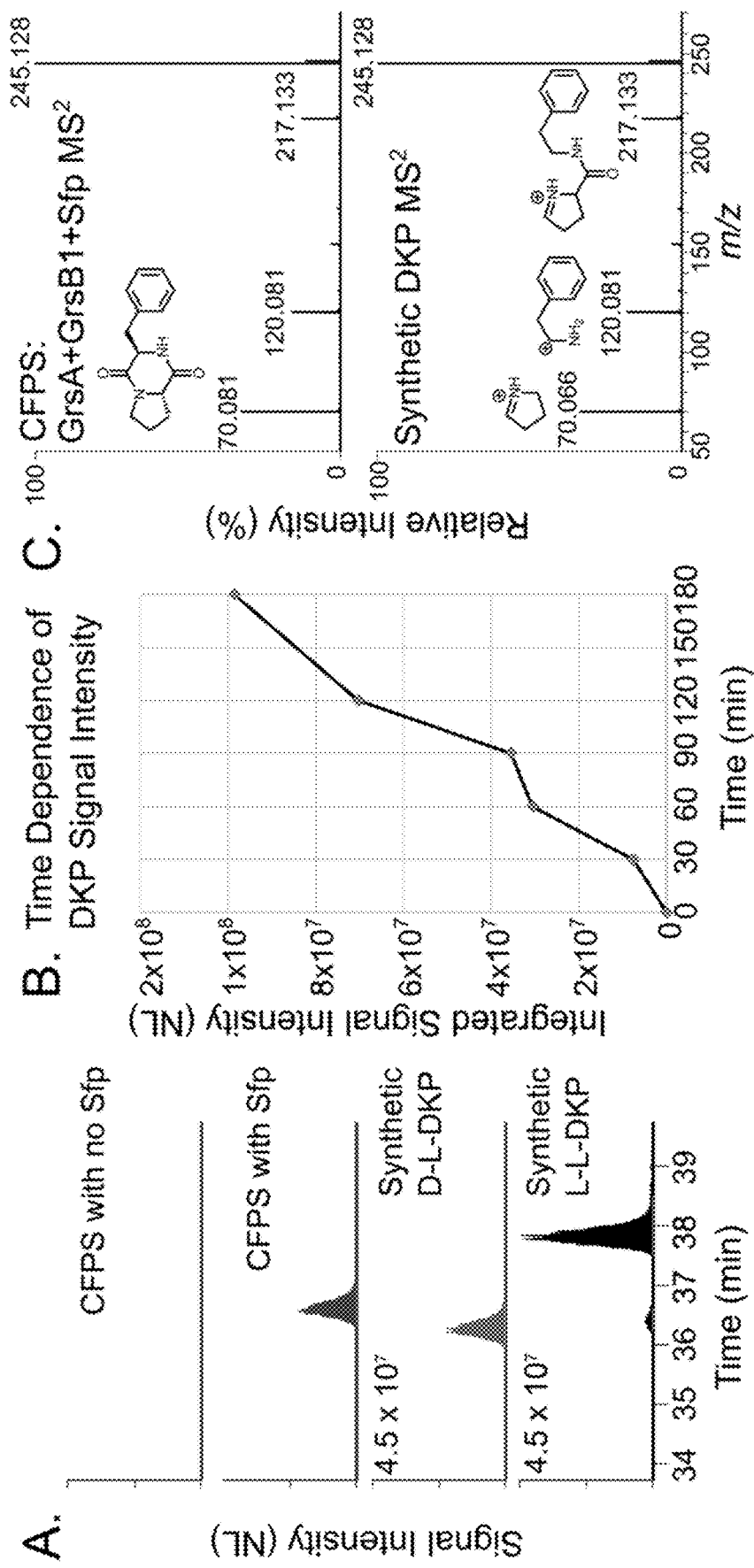

FIG. 21. Detection of D-Phe-L-Pro DKP by LC-MS/MS and comparison to synthetically prepared DKP. A) Retention time comparison of D-L, L-L and CFPS-produced DKP to determine the stereochemistry of the DKP produced by CFPS. This panel also shows that SFP is required for DKP production. B) Time dependent increase in m/z 245.128 signal after Sfp is added to the CFPS reaction. Data points are the average of two technical replicates. C) Comparison of the fragmentation pattern of the CFPS-produced (top) and synthetically prepared DKP (bottom). The spectrum at the bottom of panel C is annotated with predicted fragment ion structures.

DETAILED DESCRIPTION

Disclosed herein are systems and methods for cell-free protein synthesis driven metabolic engineering (CFPS-ME) that include cell-free protein synthesis as an integral step in the metabolic engineering process. The present invention allows for rapid prototyping and debugging of biosynthetic pathways. The present invention may also be implemented as a cell-free combinatorial method for optimization of biosynthetic pathways.

Cell-Free Protein Synthesis Driven Metabolic Engineering (CFPS-ME).

Figure 1:
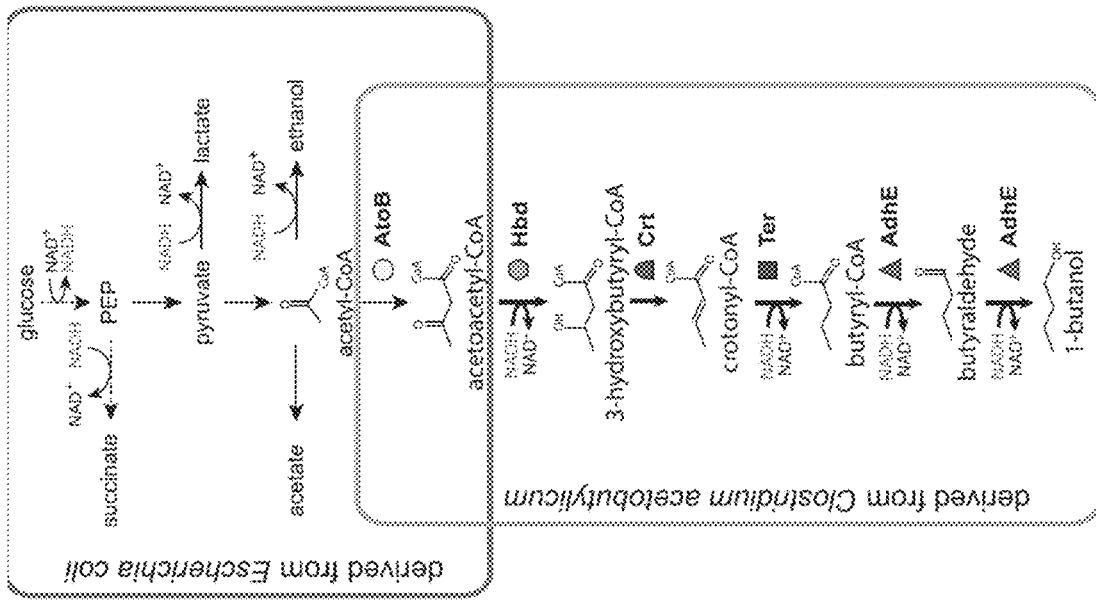
FIG. 1. A cell-free framework for pathway prototyping demonstrated with a 17-step n-butanol model pathway. (A) Methodology for cell-free metabolic engineering (CFME) and cell-free protein synthesis driven metabolic engineering (CFPS-ME). (B) Schematic (non-stoichiometric) representation of the constructed biosynthetic n-butanol pathway. Acetyl-CoA is generated through *E. coli*'s natural glycolysis and funneled into the *C. acetobutylicum*-derived CoA-dependent pathway to produce n-butanol. The butyryl-CoA dehydrogenase (Ter) here is from *Treponema denticola*. Four NADH molecules are needed to produce one molecule of n-butanol.
Figure 1:
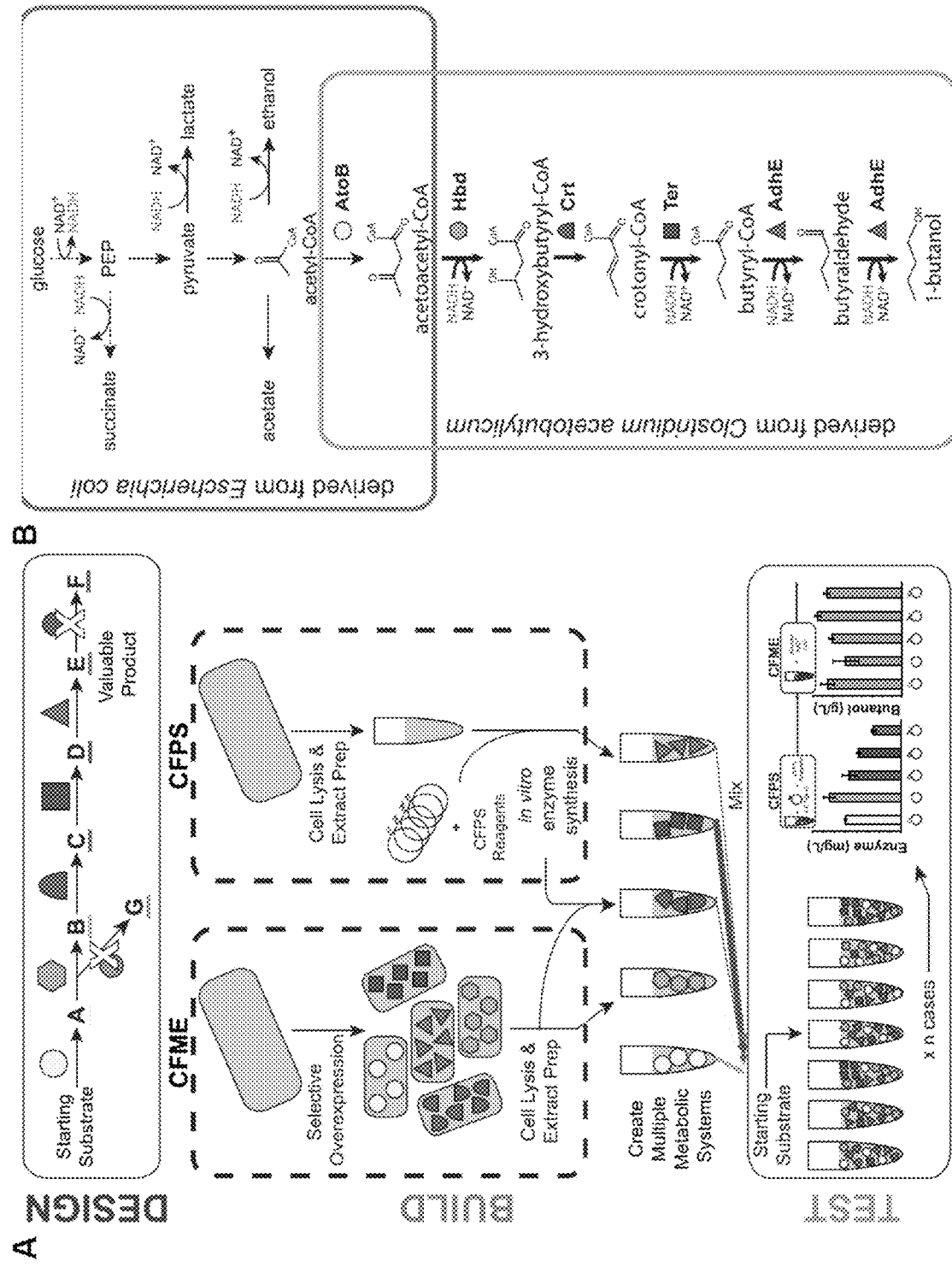

In one aspect of the invention is CFPS-ME. In one embodiment of the invention is a method for the enzymatic preparation of a chemical product in vitro. The method comprises providing a CFPS reaction mixture to a protein reaction vessel, expressing a translation template in the protein reaction vessel to prepare an enzyme, and providing the enzyme and a metabolic reaction mixture to a metabolic reaction vessel, wherein the feedstock reacts in the presence of the enzyme to prepare the chemical product. In certain embodiments, the protein reaction vessel and the metabolic reaction vessel are the same vessel. The method is illustrated in FIG. 1. Methods for cell-free protein synthesis are provided in WO/2014/144583 to Jewett et al., the disclosure of which is incorporated by reference in its entirety.

The present invention is not limited to any certain enzyme, but in certain embodiments the enzyme is selected from the group consisting of AtoB, Hbd, Crt, AdhE, and combinations thereof. The present invention is not limited to any certain feedstock, but in certain embodiments the feedstock is glucose. The present invention is not limited to any certain type of chemical product, but in certain embodiments the chemical product is 1-butanol or an intermediate in the 1-butanol biosynthetic pathway.

In certain embodiments, the method may include expressing one or more additional enzymes in a second protein reaction vessel. The second protein reaction vessel may be the same vessel as the protein reaction vessel.

In certain embodiments, the method may further comprise providing a transcription template to prepare the translation template. Where the transcription template is provided, one may additionally provide a polymerase and nucleoside triphosphates (NTPs): ATP, GTP, CTP, and UTP. Preparation of the translation template and preparation for the enzyme from the translation template may occur in the same reaction vessel or different reaction vessels.

An advantage of the present invention is that the cellular extract may provide natural enzyme metabolism from the host strain that may be exploited to perform desired chemical modifications. Natural enzyme metabolism means any process or chemical, including cellular extract enzymes, which may be necessary or beneficial for desired molecular transformations. Natural enzyme metabolism may provide energy, which may facilitate the desired molecular transformations. Natural enzyme metabolism may provide cofactor regeneration, which may facilitate the desired molecular transformation. Natural enzyme metabolism may also provide cellular extract enzymes. In certain embodiments, the cellular extract enzyme may be one or more heterologous enzymes expressed by the host. In certain embodiments, the cellular extract enzyme may be one or more native enzyme expressed by the host. In certain embodiments, the cellular extract enzyme may be a combination of one of more heterologous enzymes and native enzymes expressed by the host. In certain embodiments, the cellular extract enzyme is overexpressed by the host to enrich the extract with the cellular extract enzyme. In certain embodiments, the cellular extract enzyme may transform a chemical into a feedstock. In other embodiments, the cellular extract enzyme may further transform the chemical product that is formed by the reaction of the feedstock in the presence of the enzyme expressed by cell-free protein synthesis.

Combinatorial Approach to CFPS-ME.

The present invention, in certain embodiments, may be practiced in a combinatorial manor for rapid prototyping, design, and optimization of biosynthetic pathways. One step in the combinatorial method comprises providing N solutions. The N solutions may comprise one or more solutes. Solutes are typically chosen from those likely to be found in a CFPS reaction mixture and/or a metabolic reaction mixture. The solvent is typically buffer. It is possible that two or more of the N solutions are the same except for differences in the concentration of the solute.

Any of the solutions may be chosen to be combined, and as a result there are $2^N$ possible combinations. Selection criteria may be employed to forbid certain combinations that would limit the number of combinations to something less than $2^N$. One example of a selection criteria is to forbid the combination of two solutions that only differ in concentration of the solute.

Enzyme preparation may be initiated by combining the combinations of the N stock solutions with a CFPS reaction mixture in a cell-free protein synthesis reaction vessel to allow for the translation template to be expressed. It is not necessary for all of the combinations of the N stock salutation with a CFPS reaction mixture to result in the preparation of an enzyme because valuable information from negative results may aid the design and optimization of a biosynthetic pathway.

The method further includes providing the enzyme and a feedstock to a metabolic reaction vessel. The protein synthesis reaction vessel and the metabolic reaction vessel may be the same reaction vessel.

Kits

In one aspect of the invention, kits for CFPS-ME are disclosed. Kits for CFPS-ME comprising one or more components for the practice of the CFPS-ME method. In one aspect, the kits may comprise one or more components, individually or collectively, for the practice of CFPS. In certain embodiments, the kit may comprise a CFPS reaction mixture or the individual solutes or solutions that may be combined to form a CFPS reaction mixture. In one aspect, the kits may comprise one or more components, individually or collectively, for the practice of ME. In certain embodiments, the kit may comprise a ME reaction mixture or the individual solutes or solutions that may be combined to form a ME reaction mixture. In certain embodiments, the kit further comprises a feedstock.

Definitions

To aid in understanding the invention, several terms are defined below.

Unless defined otherwise, all technical and scientific terms used herein have the same meaning as commonly understood by one of skill in the art. Although any methods and materials similar to or equivalent to those described herein can be used in the practice or testing of the claims, the exemplary methods and materials are described herein.

Moreover, reference to an element by the indefinite article "a" or "an" does not exclude the possibility that more than one element is present, unless the context clearly requires that there be one and only one element. The indefinite article "a" or "an" thus usually means "at least one."

The term "about" means within a statistically meaningful range of a value or values such as a stated concentration, length, molecular weight, pH, time frame, temperature, pressure or volume. Such a value or range can be within an order of magnitude, typically within 20%, more typically within 10%, and even more typically within 5% of a given value or range. The allowable variation encompassed by "about" will depend upon the particular system under study.

The terms "comprising," "having," "including," and "containing" are to be construed as open-ended terms (i.e., meaning "including, but not limited to,") unless otherwise noted.

Recitation of ranges of values herein are merely intended to serve as a shorthand method of referring individually to each separate value falling within the range, and includes the endpoint boundaries defining the range, unless otherwise indicated herein, and each separate value is incorporated into the specification as if it were individually recited herein.

The terms "nucleic acid" and "oligonucleotide," as used herein, refer to polydeoxyribonucleotides (containing 2-deoxy-D-ribose), polyribonucleotides (containing D-ribose), and to any other type of polynucleotide that is an N glycoside of a purine or pyrimidine base. There is no intended distinction in length between the terms "nucleic acid", "oligonucleotide" and "polynucleotide", and these terms will be used interchangeably. These terms refer only to the primary structure of the molecule. Thus, these terms include double- and single-stranded DNA, as well as double- and single-stranded RNA. For use in the present invention, an oligonucleotide also can comprise nucleotide analogs in which the base, sugar or phosphate backbone is modified as well as non-purine or non-pyrimidine nucleotide analogs.

Oligonucleotides can be prepared by any suitable method, including direct chemical synthesis by a method such as the phosphodiester method of Narang et al., 1979, Meth. Enzymol. 68:90-99; the phosphodiester method of Brown et al., 1979, Meth. Enzymol. 68:109-151; the diethylphosphoramidite method of Beaucage et al., 1981, Tetrahedron Letters 22:1859-1862; and the solid support method of U.S. Pat. No. 4,458,066, each incorporated herein by reference. A review of synthesis methods of conjugates of oligonucleotides and modified nucleotides is provided in Goodchild, 1990, Bioconjugate Chemistry 1(3): 165-187, incorporated herein by reference.

The term "primer," as used herein, refers to an oligonucleotide capable of acting as a point of initiation of DNA synthesis under suitable conditions. Such conditions include those in which synthesis of a primer extension product complementary to a nucleic acid strand is induced in the presence of four different nucleoside triphosphates and an agent for extension (for example, a DNA polymerase or reverse transcriptase) in an appropriate buffer and at a suitable temperature.

A primer is preferably a single-stranded DNA. The appropriate length of a primer depends on the intended use of the primer but typically ranges from about 6 to about 225 nucleotides, including intermediate ranges, such as from 15 to 35 nucleotides, from 18 to 75 nucleotides and from 25 to 150 nucleotides. Short primer molecules generally require cooler temperatures to form sufficiently stable hybrid complexes with the template. A primer need not reflect the exact sequence of the template nucleic acid, but must be sufficiently complementary to hybridize with the template. The design of suitable primers for the amplification of a given target sequence is well known in the art and described in the literature cited herein.

Primers can incorporate additional features which allow for the detection or immobilization of the primer but do not alter the basic property of the primer, that of acting as a point of initiation of DNA synthesis. For example, primers may contain an additional nucleic acid sequence at the 5' end which does not hybridize to the target nucleic acid, but which facilitates cloning or detection of the amplified product, or which enables transcription of RNA (for example, by inclusion of a promoter) or translation of protein (for example, by inclusion of a 5'-UTR, such as an Internal Ribosome Entry Site (IRES) or a 3'-UTR element, such as a poly(A)n sequence, where n is in the range from about 20 to about 200). The region of the primer that is sufficiently complementary to the template to hybridize is referred to herein as the hybridizing region.

The term "promoter" refers to a cis-acting DNA sequence that directs RNA polymerase and other trans-acting transcription factors to initiate RNA transcription from the DNA template that includes the cis-acting DNA sequence.

The terms "target, "target sequence", "target region", and "target nucleic acid," as used herein, are synonymous and refer to a region or sequence of a nucleic acid which is to be amplified, sequenced or detected.

The term "hybridization," as used herein, refers to the formation of a duplex structure by two single-stranded nucleic acids due to complementary base pairing. Hybridization can occur between fully complementary nucleic acid strands or between "substantially complementary" nucleic acid strands that contain minor regions of mismatch. Conditions under which hybridization of fully complementary nucleic acid strands is strongly preferred are referred to as "stringent hybridization conditions" or "sequence-specific hybridization conditions". Stable duplexes of substantially complementary sequences can be achieved under less stringent hybridization conditions; the degree of mismatch tolerated can be controlled by suitable adjustment of the hybridization conditions. Those skilled in the art of nucleic acid technology can determine duplex stability empirically considering a number of variables including, for example, the length and base pair composition of the oligonucleotides, ionic strength, and incidence of mismatched base pairs, following the guidance provided by the art (see, e.g., Sambrook et al., 1989, Molecular Cloning—A Laboratory Manual, Cold Spring Harbor Laboratory, Cold Spring Harbor, N.Y.; Wetmur, 1991, Critical Review in Biochem. and Mol. Biol. 26(3/4):227-259; and Owczarzy et al., 2008, Biochemistry, 47: 5336-5353, which are incorporated herein by reference).

The term "amplification reaction" refers to any chemical reaction, including an enzymatic reaction, which results in increased copies of a template nucleic acid sequence or results in transcription of a template nucleic acid. Amplification reactions include reverse transcription, the polymerase chain reaction (PCR), including Real Time PCR (see U.S. Pat. Nos. 4,683,195 and 4,683,202; PCR Protocols: A Guide to Methods and Applications (Innis et al., eds, 1990)), and the ligase chain reaction (LCR) (see Barany et al., U.S. Pat. No. 5,494,810). Exemplary "amplification reactions conditions" or "amplification conditions" typically comprise either two or three step cycles. Two-step cycles have a high temperature denaturation step followed by a hybridization/elongation (or ligation) step. Three step cycles comprise a denaturation step followed by a hybridization step followed by a separate elongation step.

As used herein, a "polymerase" refers to an enzyme that catalyzes the polymerization of nucleotides. "DNA polymerase" catalyzes the polymerization of deoxyribonucleotides. Known DNA polymerases include, for example, *Pyrococcus furiosus* (Pfu) DNA polymerase, *E. coli* DNA polymerase I, T7 DNA polymerase and *Thermus aquaticus* (Taq) DNA polymerase, among others. "RNA polymerase" catalyzes the polymerization of ribonucleotides. The foregoing examples of DNA polymerases are also known as DNA-dependent DNA polymerases. RNA-dependent DNA polymerases also fall within the scope of DNA polymerases. Reverse transcriptase, which includes viral polymerases encoded by retroviruses, is an example of an RNA-dependent DNA polymerase. Known examples of RNA polymerase ("RNAP") include, for example, T3 RNA polymerase, T7 RNA polymerase, SP6 RNA polymerase and *E. coli* RNA polymerase, among others. The foregoing examples of RNA polymerases are also known as DNA-dependent RNA polymerase. The polymerase activity of any of the above enzymes can be determined by means well known in the art.

As used herein, a primer is "specific," for a target sequence if, when used in an amplification reaction under sufficiently stringent conditions, the primer hybridizes primarily to the target nucleic acid. Typically, a primer is specific for a target sequence if the primer-target duplex stability is greater than the stability of a duplex formed between the primer and any other sequence found in the sample. One of skill in the art will recognize that various factors, such as salt conditions as well as base composition of the primer and the location of the mismatches, will affect the specificity of the primer, and that routine experimental confirmation of the primer specificity will be needed in many cases. Hybridization conditions can be chosen under which the primer can form stable duplexes only with a target sequence. Thus, the use of target-specific primers under suitably stringent amplification conditions enables the selective amplification of those target sequences that contain the target primer binding sites.

As used herein, "expression template" refers to a nucleic acid that serves as substrate for transcribing at least one RNA that can be translated into a polypeptide or protein. Expression templates include nucleic acids composed of DNA or RNA. Suitable sources of DNA for use a nucleic acid for an expression template include genomic DNA, cDNA and RNA that can be converted into cDNA. Genomic DNA, cDNA and RNA can be from any biological source, such as a tissue sample, a biopsy, a swab, sputum, a blood sample, a fecal sample, a urine sample, a scraping, among others. The genomic DNA, cDNA and RNA can be from host cell or virus origins and from any species, including extant and extinct organisms. As used herein, "expression template" and "transcription template" have the same meaning and are used interchangeably.

As used herein, "translation template" refers to an RNA product of transcription from an expression template that can be used by ribosomes to synthesize polypeptide or protein.

The term "reaction mixture," as used herein, refers to a solution containing reagents necessary to carry out a given reaction. A reaction mixture is referred to as complete if it contains all reagents necessary to enable the reaction, and incomplete if it contains only a subset of the necessary reagents.

An "amplification reaction mixture", which refers to a solution containing reagents necessary to carry out an amplification reaction, typically contains oligonucleotide primers and a DNA polymerase in a suitable buffer.

A "PCR reaction mixture", which refers to a solution containing the reagents necessary to carry out a PCR reaction, typically contains DNA polymerase, dNTPs, and a divalent metal cation in a suitable buffer.

A "cell-free protein synthesis (CFPS) reaction mixture", which refers to a solution containing the reagents necessary to carry out CFPS, typically contains a crude or partially-purified yeast extract, an RNA translation template, and a suitable reaction buffer for promoting cell-free protein synthesis from the RNA translation template. In some aspects, the CFPS reaction mixture can include exogenous RNA translation template. In other aspects, the CFPS reaction mixture can include a DNA expression template encoding an open reading frame operably linked to a promoter element for a DNA-dependent RNA polymerase. In these other aspects, the CFPS reaction mixture can also include a DNA-dependent RNA polymerase to direct transcription of an RNA translation template encoding the open reading frame. In these other aspects, additional NTP's and divalent cation cofactor can be included in the CFPS reaction mixture A "metabolic reaction mixture", which refers to a solution containing the reagents necessary to carry out an enzyme-mediated metabolic or biosynthetic step, typically includes a feedstock that reacts in the presence of the enzyme to produce a final or intermediate product in the metabolic or biosynthetic pathway. A metabolic reaction mixture may optionally contain a cofactor, e.g. coenzyme-A, NAD, or ATP, or a buffer.

It will be understood by one of ordinary skill in the art that reaction components are routinely stored as separate solutions, each containing a subset of the total components, for reasons of convenience, storage stability, or to allow for application-dependent adjustment of the component concentrations, and that reaction components are combined prior to the reaction to create a complete reaction mixture. Furthermore, it will be understood by one of ordinary skill in the art that reaction components are packaged separately for commercialization and that useful commercial kits may contain any subset of the reaction components of the invention.

Miscellaneous.

All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred aspects of this invention are described herein, including the best mode known to the inventors for carrying out the invention. Variations of those preferred aspects may become apparent to those of ordinary skill in the art upon reading the foregoing description. The inventors expect a person having ordinary skill in the art to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

EXAMPLES

The following examples are illustrative and should not be interpreted to limit the scope of the claimed subject matter.

Reference is made to Karim and Jewett, "A cell-free framework for rapid biosynthetic pathway prototyping and enzyme discovery," (Metab. Eng. March 17; 36:116-126, doi: 10.1016/j.ymben.2016.03.002. [Epub ahead of print], hereinafter "Karim 2016")), the content of which is incorporated herein by reference in its entirety.

Abstract

Speeding up design-build-test (DBT) cycles is a fundamental challenge facing biochemical engineering. To address this challenge, we report a new cell-free protein synthesis driven metabolic engineering (CFPS-ME) framework for rapid biosynthetic pathway prototyping. In our framework, cell-free cocktails for synthesizing target small molecules are assembled in a mix-and-match fashion from crude cell lysates either containing selectively enriched pathway enzymes from heterologous overexpression or directly producing pathway enzymes in lysates by CFPS. As a model, we apply our approach to n-butanol biosynthesis showing that *Escherichia coli* lysates support a highly active 17-step CoA-dependent n-butanol pathway in vitro. The elevated degree of flexibility in the cell-free environment allows us to manipulate physiochemical conditions, access enzymatic nodes, discover new enzymes, and prototype enzyme sets with linear DNA templates to study pathway performance. We anticipate that CFPS-ME will facilitate efforts to define, manipulate, and understand metabolic pathways for accelerated DBT cycles without the need to reengineer organisms. Highlights of CFPS-ME include the following: Cell-free protein synthesis can reconstitute entire biosynthetic pathways (CFPS-ME); In vitro systems provide greater control and higher resolution in studying metabolism; CFPS-ME enables the in vitro study of pathways in context of native metabolism; Linear DNA with CFPS-ME can bypass in vivo cloning steps in pathway construction; and CFPS-ME allows rapid enzyme prototyping in vitro before putting designs into a host.

Introduction

For decades scientists and engineers have turned to engineering biological systems to help meet societal needs in energy, medicine, materials, and more[1-4]. This has been an attractive, sustainable way to produce small molecules, especially when chemical synthesis is untenable[5,6]. The ability to harness organisms that naturally produce molecules of interest has expanded the available chemical palate[7,8]. Often when natural producers are insufficient for production at the optimal titer (g $l^{-1}$), yield, or volumetric productivity (g $l^{-1}$ $h^{-1}$), engineers seek to design biosynthetic pathways and regulatory processes in cells to meet certain manufacturing criteria[9,10]. For example, introducing heterologous pathways into model microorganisms and engineering them to maximize a particular biosynthesis has led to large scale production of 1,3-propanediol, farnesene, and artemisinin with many more on their way to market[6,11]. Efforts to make these molecules have resulted in success, but not without a great deal of challenges.

Bringing a biosynthetic molecule to market usually involves countless hours of design-build-test (DBT) cycles[12]. The production of n-butanol is a prime example of these challenges. A series of Clostridia species are natural producers of n-butanol during acetone-butanol-ethanol fermentation, and Clostridia acetobutylicum and Clostridia beijerinckii are two of which are commonly used in commercial n-butanol plants[13]. However, these species are difficult to engineer because of a biphasic metabolism, unknown regulation patterns, and a limited number of species-specific engineering tools[14]. Heterologous expression of Clostridia metabolism in model microorganisms like Escherichia coli and Saccharomyces cerevisiae allows n-butanol production to be more easily engineered but can be accompanied by lower titers[15,16]. Starting with heterologous expression of the n-butanol pathway as a baseline, scientists have been able to increase titers dramatically by knocking out genes from genomes[15], increasing redox driving forces by introducing pathway-independent enzymes[17], and identifying homologous enzymes with better activities[18]. Years of iterative metabolic engineering led to these advances, but titers are still not high enough and scale-up is often too unpredictable to outcompete natural producers for commercial production[19]. As is the same for many biosynthetic pathways, we cannot quickly enough identify optimal biosynthetic systems and discover the best sets of enzymes that work together as a group. Therefore, metabolic engineering remains costly and time-consuming[20,21].

A key challenge in metabolic engineering is balancing the tug-of-war that exists between the cell's physiological and evolutionary objectives on one side and the engineer's process objectives on the other. Put another way, it is very difficult to balance intracellular fluxes to optimally satisfy a very active synthetic pathway while the machinery of the cell is functioning to maintain reproductive viability. Other challenges include: (i) the need for reliable computational selection and design of enzyme homologs for pathway design, (ii) the limited number of feasible homologs and genetic constructs that can be searched in any one project, and (iii) the unknown effects of optimal pathway enzyme expression on the entire metabolic system[22-24].

Many established and emerging technologies seek to address these challenges. For example, metabolic flux analysis and genome engineering offer generalized capabilities to modify living organisms for improving product titers[25,26]. In addition, coupling machine-learning algorithms to multiplexed designs can accelerate efforts to rationally engineer cells[27]. However, DBT cycle time remains a limitation[28]. In vitro systems offer a complementary, yet underutilized approach to speed up DBT cycles with some potential advantages[11,29-31]. For example, the open reaction environment allows for the addition of components such as cofactors and intermediates at any time during a cell-free reaction, which can be maintained at precise concentrations. In addition, cell-free systems have no cell viability constraints. Furthermore, the cell-free format permits DBT iterations without the need to reengineer organisms[30], with the potential to reduce DBT cycle time[31]. Cell-free metabolic engineering (CFME), or using cell-free techniques to aid metabolic engineering efforts, is emerging as a complementary approach to existing strategies for carrying out biomolecular transformations of interest with in vitro ensembles of catalytic proteins, prepared from purified enzymes or crude lysates of cells[32-39].

In this work, we develop a cell-free protein synthesis driven metabolic engineering (CFPS-ME) framework to accelerate DBT cycles for optimizing and debugging biosynthetic pathways (FIG. 1A). The foundational principle is that we can construct discrete metabolic pathways through combinatorial and modular assembly of lysates containing enzyme components produced by overexpression in the lysate chassis strain or by cell-free protein synthesis (CFPS). We focus on using CFPS because these systems can help address the growing demand for simple, inexpensive, and efficient protein production technologies for a wide array of applications[11,29,40-44]. In addition, processes that take days or weeks to design, prepare, and execute in cells can be done more rapidly in a cell-free system, because no time-consuming cloning steps are needed[45]. Three recent advances enable the use of CFPS for CFME. First, Jewett et al. demonstrated the ability to stimulate highly active energy and cofactor regeneration pathways in crude cell lysates[46]. Second, Kay and Jewett showed that crude cell lysate based cell-free systems from E. coli could fuel highly active heterologous metabolic transformations[36]. Third, Dudley and Jewett established the ability to build a heterologous biosynthetic pathway by mixing lysates each containing individually overexpressed heterologous enzymes (in preparation). The mix-and-match approach has many advantages including only needing to express one enzyme in each strain, not needing to fine-tune expression, and being able to directly monitor and sample the reaction environment. Here, we extend this approach by demonstrating modular assembly of pathways through the ability to enrich lysates with biosynthetic enzymes using well-defined experimental conditions and CFPS. It is important to note that our goal in this work was not to develop cell-free systems for the highest product titer, an engineered strain for best in vivo synthesis of n-butanol, or industrial applicability. However, we do show that CFPS-ME offers an even faster approach (hours rather than days) for building pathways directly in lysates for the purpose of enzyme selection and pathway design.

To demonstrate CFPS-ME, we selected the model n-butanol biosynthetic pathway derived from Clostridia metabolism involving CoA intermediates (FIG. 1B). Endogenous glycolytic enzymes convert glucose to acetyl-CoA, the starting intermediate for n-butanol synthesis, another E. coli enzyme takes acetyl-CoA to acetoacetyl-CoA, and heterologous enzymes convert acetoacetyl-CoA to n-butanol. We first show the ability to mix five crude lysates each with selectively overexpressed enzymes to activate the entire 17-step n-butanol production pathway in vitro with high yield and productivities. We then establish the CFPS-ME concept by modularly building the n-butanol pathway with lysates harboring heterologous pathway enzymes expressed by CFPS or having been overexpressed in the chassis source strain. We apply this framework to rapidly screen enzymes for optimal pathway operation and enzyme discovery. We expect that the CFPS-ME framework will increase the resolution at which we can manipulate biosynthetic pathways by examining enzyme kinetics, measuring metabolic flux, determining catalyst stability, studying redox effects, and prototyping metabolism.

Material and Methods 2.1 Bacterial Strains and Plasmids.

*E. coli* NEB Turbo™ (NEB) was used in plasmid cloning transformations and for plasmid preparation. *E. coli* BL21 (DE3) (NEB) was used for protein overexpression and for preparation of all extracts. (See Karim 2016, and Table 1 for strain details). A modified version of pET-22b (Novagen/EMD Millipore), used in previous studies[36], was used for all constructs for in vivo over-expression of proteins. For in vitro expression of proteins, the pJL1 vector was used. Carbenicillin (100 µg ml$^{-1}$) was used with the pET vector system and kanamycin (50 µg ml$^{-1}$) was used with the pJL1 vector system.

Gibson assembly was used for seamless construction of plasmids. (See Karim 2016, and Table 1 for plasmid details) Each gene and vector was amplified via PCR using forward and reverse primers designed with NEB's Gibson Assembly Designer (New England Biolabs, Ipswich Mass., USA) and purchased from IDT and Phusion® High-Fidelity DNA polymerase (Finnzymes, Thermo Scientific Molecular Biology). (See Karim 2016, and Table 2 for genes and enzymes and Karim 2016 for primer details). Both PCR products were cleaned and mixed with Gibson assembly reactants and incubated at 50° C. for 60 min. Plasmid DNA from the Gibson assembly reactions were immediately transformed into *E. coli* NEB Turbo cells. Propagated constructs were purified using an EZNA Plasmid Mini Kit (Omega Bio-Tek). Completed constructs were used to transform *E. coli* BL21 (DE3).

Codon optimized versions of each gene were identified using IDT's codon optimization online tool (Integrated DNA Technologies®, Coralville, USA) and NCBI's Basic Local Alignment Search Tool (National Center for Biotechnology Information, U.S. National Library of Medicine, Bethesda Md., USA). These genes were purchased from Gen9, Inc. (Cambridge Mass., USA). (See Karim 2016, and SEQ ID NOs:1-18).

2.2 Cell Extract Preparation.

*E. coli* BL21(DE3) cells (see Karim 2016 and Table 1 for strains) were grown in 2×YTPG media (16 g l$^{-1}$ tryptone, 10 g l$^{-1}$ yeast extract, 5 g l$^{-1}$ NaCl, 7 g l$^{-1}$ potassium phosphate monobasic, 3 g l$^{-1}$ potassium phosphate dibasic, 18 g l$^{-1}$ glucose). These cells were cultured at the 50 ml scale in 250 ml baffled tunair shake flasks (IBI Scientific, Peosta, Iowa) in a 37° C. incubator with vigorous shaking at 250 rpm. The cultured cells were monitored by spectrophotometry (Genesys 10S UV-Vis, Thermo Fisher Scientific, Waltham, Mass.). When cells reached $OD_{600}$=0.6-0.8, the cultures were induced with 0.1 mM IPTG. After induction cultures were grown for 4 h at 30° C. Antibiotics were not used during cell growth. The cells were harvested by centrifuging at 8,000 g at 4° C. for 15 min and were washed two times with cold S30 buffer (10 mM Tris-acetate (pH 8.2), 14 mM magnesium acetate, and 60 mM potassium glutamate). After final wash and centrifugation, the pelleted wet cells were weighed, flash frozen in liquid nitrogen, and stored at −80° C. The thawed cells were suspended in 0.8 ml of S30 buffer per 1 g of wet cell mass. In order to lyse cells by sonication, thawed and suspended cells were transferred into 1.5 ml microtube and placed in an ice-water bath to minimize heat damage during sonication. The cells were lysed using a Q125 Sonicator (Qsonica, Newtown, Conn.) with 3.175 mm diameter probe at frequency of 20 kHz and 50% of amplitude. The input energy (Joules) was monitored and 830 J was used for 1.4 ml of suspended cells. The lysate was then centrifuged twice at 21,100 g at 4° C. for 15 min. All of prepared cell extract was flash frozen in liquid nitrogen and stored at −80° C. until use.

2.3 Extract Protein Quantification.

The total protein concentration of the extracts was measured by Quick-Start Bradford protein assay kits (Bio-Rad) with a bovine serum albumin standard. The extracts were subsequently run on a Coomassie-blue stained NuPAGE Bis-Tris 12% SDS-PAGE gel with MOPS buffer (Life Technology, Grand Island, N.Y.). The SeeBlue Plus2 prestained ladder (Life Technology, Grand Island, N.Y.) was used and ~10 µg of total protein for each sample was loaded on the gel.

2.4 CFME Reactions.

Reactions were carried out in 1.5 ml Eppendorf tubes at 37° C. in 25 µl volumes. Each reaction consisted of mixing five extracts, containing one enzyme overexpressed each, to complete the biosynthetic n-butanol pathway (2 mg ml$^{-1}$) along with magnesium glutamate (8 mM), ammonium glutamate (10 mM), potassium glutamate (134 mM), glucose (200 mM), dipotassium phosphate (10 mM, pH 7.2), Bis Tris (100 mM), NAD (1 mM), ATP (1 mM), and CoA (0.5 mM), unless otherwise noted. Reactions were terminated by adding 5% w/v trichloroacetic acid in a 1:1 ratio. Precipitated proteins were pelleted by centrifugation at 15,000 g for 10 min. The supernatant was stored at −80° C. until analysis.

2.5 CFPS-ME Reactions.

CFPS reactions were performed to express enzymes involved in n-butanol production prior to starting the CFME portion of the reactions using a modified PANOx-SP system[47]. A 25 µl CFPS reaction in a 1.5 ml microcentrifuge tube was prepared by mixing the following components: ATP (1.2 mM); GTP, UTP, and CTP (0.85 mM each); folinic acid (34.0 µg ml$^{-1}$); *E. coli* tRNA mixture (170.0 µg ml$^{-1}$); T7 RNA polymerase (100 µg ml$^{-1}$); 20 standard amino acids (2 mM each); nicotinamide adenine dinucleotide (NAD; 0.33 mm); coenzyme-A (0.27 mM); spermidine (1.5 mM); putrescine (1 mM); potassium glutamate (130 mM); ammonium glutamate (10 mM); magnesium glutamate (12 mM); phosphoenolpyruvate (PEP; 33 mM), and cell extract (10 mg ml$^{-1}$). For each reaction plasmid was added at ~13.3 or ~26.6 µg ml$^{-1}$. The n-butanol production portion of the reaction was initiated by spiking in glucose (200 mM) and additional reagents (NAD, CoA) noted throughout the manuscript.

2.6 Quantification of Protein Produced In Vitro.

Cell-free protein synthesis reactions were performed as noted above (Section 2.5) with radioactive $^{14}$C-Leucine (10 µM) supplemented in addition to all 20 standard amino acids. We used trichloroacetic acid (TCA) to precipitate radioactive protein samples. Radioactivity of TCA-precipitated samples was measured by liquid scintillation counting to then quantify the protein produced as previously reported (MicroBeta2; PerkinElmer)[46,47]. These reactions were also run on a Coomassie-stained SDS-PAGE gel and exposed by autoradiography. Autoradiographs were imaged with a Typhoon 7000 (GE Healthcare Life Sciences, Pittsburgh, Pa.). Multiple proteins produced in vitro were further quantified by gel image intensity comparisons using ImageJ (NIH).

2.7 n-Butanol Quantification.

High-performance liquid chromatography (HPLC) was used to analyze the components in the reactions. n-Butanol was measured with an Agilent 1260 series HPLC system (Agilent, Santa Clara, Calif.) via a refractive index (RD detector. Analytes were separated using the Aminex HPX-87H anion exchange column (Bio-Rad Laboratories) with a 5 mM sulfuric acid mobile phase at 55° C. and a flow rate of 0.6 ml min$^{-1}$. Commercial standard of n-butanol was used for quantification of experimental samples by linear interpolation of external standard curves. An example chromatogram for n-butanol is given in FIG. 7.

Results

In developing a framework for biosynthetic pathway prototyping, we constructed a 17-step pathway for the production of n-butanol. n-butanol synthesis was selected as a model because of its importance as a potential biofuel, it is easily quantified by HPLC, and it has multiple heterologous steps. We sought to combine E. coli's endogenous 11-step glycolytic pathway from glucose to acetyl-CoA (AcCoA) with the Clostridia-derived six-step n-butanol pathway from AcCoA (FIG. 1B). The idea that natural energy and cofactor regeneration would be harnessed in the lysate to fuel n-butanol production is a distinct break from typical in vitro approaches, which use purified enzymes[32]. Complementary to those systems, our approach allows for studying pathway performance in a setting that better mimics the in vivo operation (e.g., from glucose rather than AcCoA). The crude lysate system also allows us to focus on expressing only the necessary heterologous enzymes to complete the entire pathway. These enzymes include a thiolase to merge two AcCoAs followed by a number of dehydrogenases to perform a series of reductions through CoA intermediates to obtain n-butanol (See Karim 2016, and Table 2 for Genes and Enzymes).

3.1 Cell-Free Metabolic Engineering for n-Butanol Production.

Figure 2:
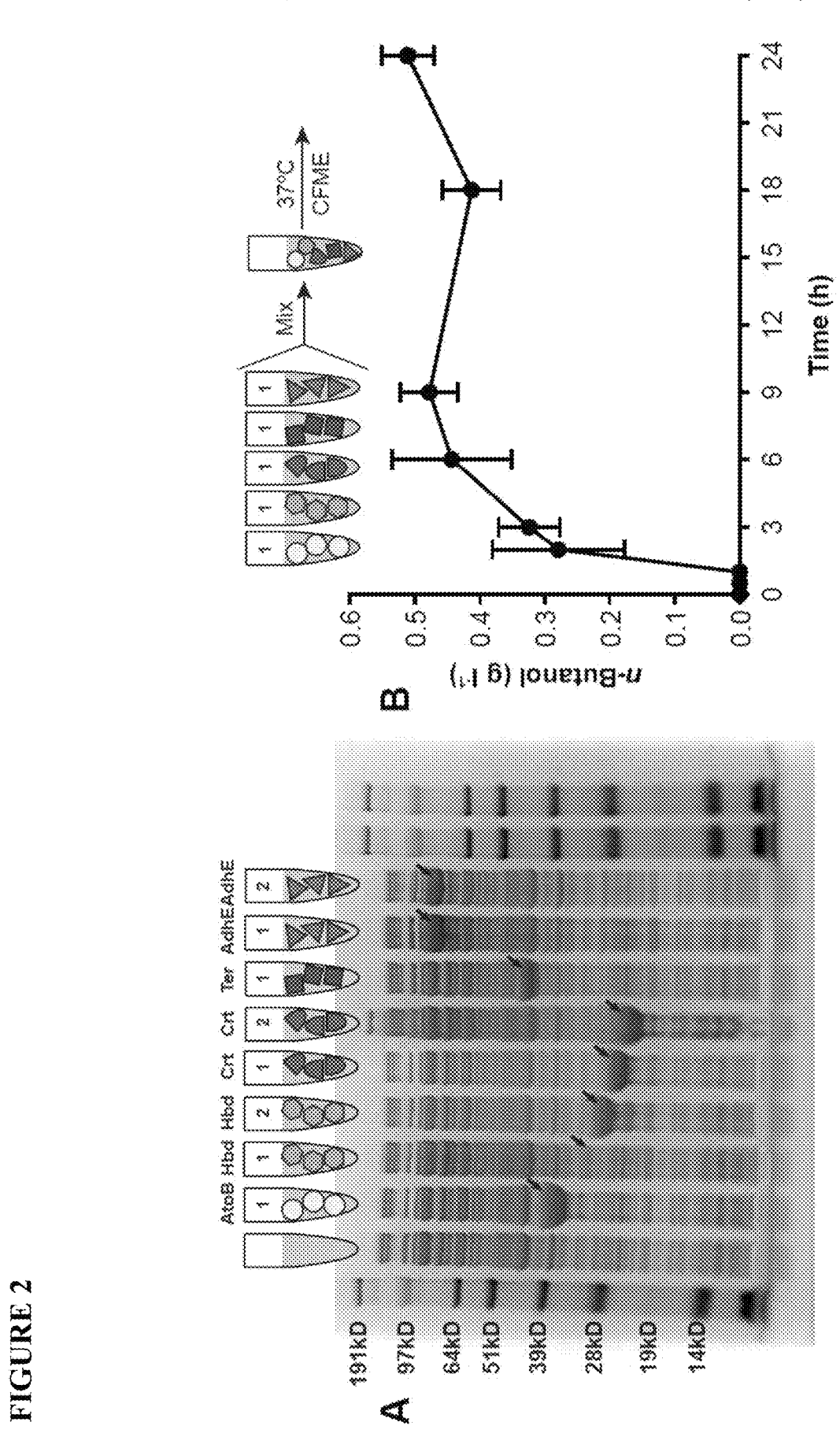
FIG. 2. Biosynthesis of n-butanol achieved via CFME of a coupled *E. coli* and *C. acetobutylicum* metabolic pathway. (A) Via SDS-PAGE, the gel verifies the selective overexpression of pathway enzymes in *E. coli* BL21(DE3) crude cell lysates: AtoB (*Escherichia coli*), Hbd1 (*Clostridia acetobutylicum*, CA), Hbd2 (*Clostridia beijerinckii*, CB), Crt1 (*Clostridium acetobutylicum*, CA), Crt2 (*Pseudomonas putida*, PP), Ter (*Treponema denticola*, TD), AdhE1 (*Clostridium acetobutylicum*, CA), and AdhE2 (*Clostridium pasteurianum*, CP). (B) CFME reactions for n-butanol production from glucose were carried out using five crude lysates mixed together (1:1:1:1:1 based on total protein quantification) with glutamate salts ($Mg^+$, $NH_4^+$, $K^+$), phosphate ($K_2HPO_4$), buffer (Bis Tris), and cofactors (ATP, CoA, $NAD^+$). These lysates individually contained AtoB (EC), Hbd1 (CA), Crt1 (CA), Ter1 (TD), and AdhE1 (CA) selectively overexpressed at 37° C. Error bars represent standard deviations with $n \geq 3$ independent reactions.

To enable cell-free biosynthesis of n-butanol, we first introduced genes encoding the five enzymes needed to convert AcCoA to n-butanol individually into our extract source strains, in this case BL21(DE3) (See Karim 2016, Table 1 for Strains and Plasmids, and Karim 2016 for Primers). We selected two homologs each for hydroxybutyryl-CoA dehydrogenase (Hbd), crotonase (Crt), and bifunctional aldehyde/alcohol dehydrogenase functionalities. For the thiolase (AtoB) and butyryl-CoA dehydrogenase (Ter) we chose E. coli's endogenous enzyme and a widely used enzyme from Treponema denticola, respectively. Next, we selectively overexpressed each heterologous enzyme in separate strains using a tightly controlled T7 promoter and strong ribosome binding site. As expected, we observed that the heterologous proteins were overexpressed as the dominant bands, with the exception of Hbd1, on an SDS-PAGE gel (FIG. 2A). The low expression of Hbd1 is likely due to RBS used for expression.

After lysis and extract preparation, we then reconstituted the 17-step pathway from glucose to n-butanol by mixing equal total protein concentrations of five separate extracts containing each enzyme. Specifically, we started with the following enzyme set: E. coli's AtoB, C. acetobutylicum's Hbd, Crt, and AdhE2, as well as Ter from T. denticola. This set was chosen to include most of C. acetobutylicum's enzyme set, one of the most widely used sets for n-butanol production, along with previously identified best enzymes for thiolase and butyryl-CoA dehydrogenase functions[17,19]. Upon incubation with essential substrates, salts, and cofactors (e.g., magnesium, potassium, and ammonium salts, glucose, phosphate, buffer, NAD, CoA, ATP), we assessed n-butanol synthesis in 25 μl CFME batch reactions carried out for 24 h at 37° C. via high performance liquid chromatography (HPLC). We observed production of 0.51±0.04 g l$^{-1}$ n-butanol (~0.05 mol n-butanol/mol glucose) over the course of a 24 h reaction (FIG. 2B), without any optimization to improve titers. As expected, we also observed lactate, acetate, and ethanol as byproducts seen in previous reports of n-butanol production, which could be addressed through genome modifications (e.g., deletion of ldh gene in the source strain)[19]. Butanol production shows that both the heterologous pathway and endogenous glycolysis is activated with cofactors being regenerated. However, n-butanol production stops after ~9 h. In previous work, substrate depletion was shown to be the most typical cause for reaction termination[36]. One way to avoid this limitation is to run reactions in fed-batch or continuous reactor set-ups or use substrates that are metabolized slower (e.g. polymeric sugars). Except in few instances[39,48], limited cofactor regeneration has historically plagued in vitro synthetic enzymatic pathway conversions[32,34,35]. Here, however, native glycolytic enzymes in the lysate provide a simple route to fuel highly active heterologous metabolic conversions. For example, to produce ~7 mM n-butanol we would need ~56 NADH turnover events, exceeding typical turnover numbers of ~5-20 for purified in vitro systems[32].

Figure 3:
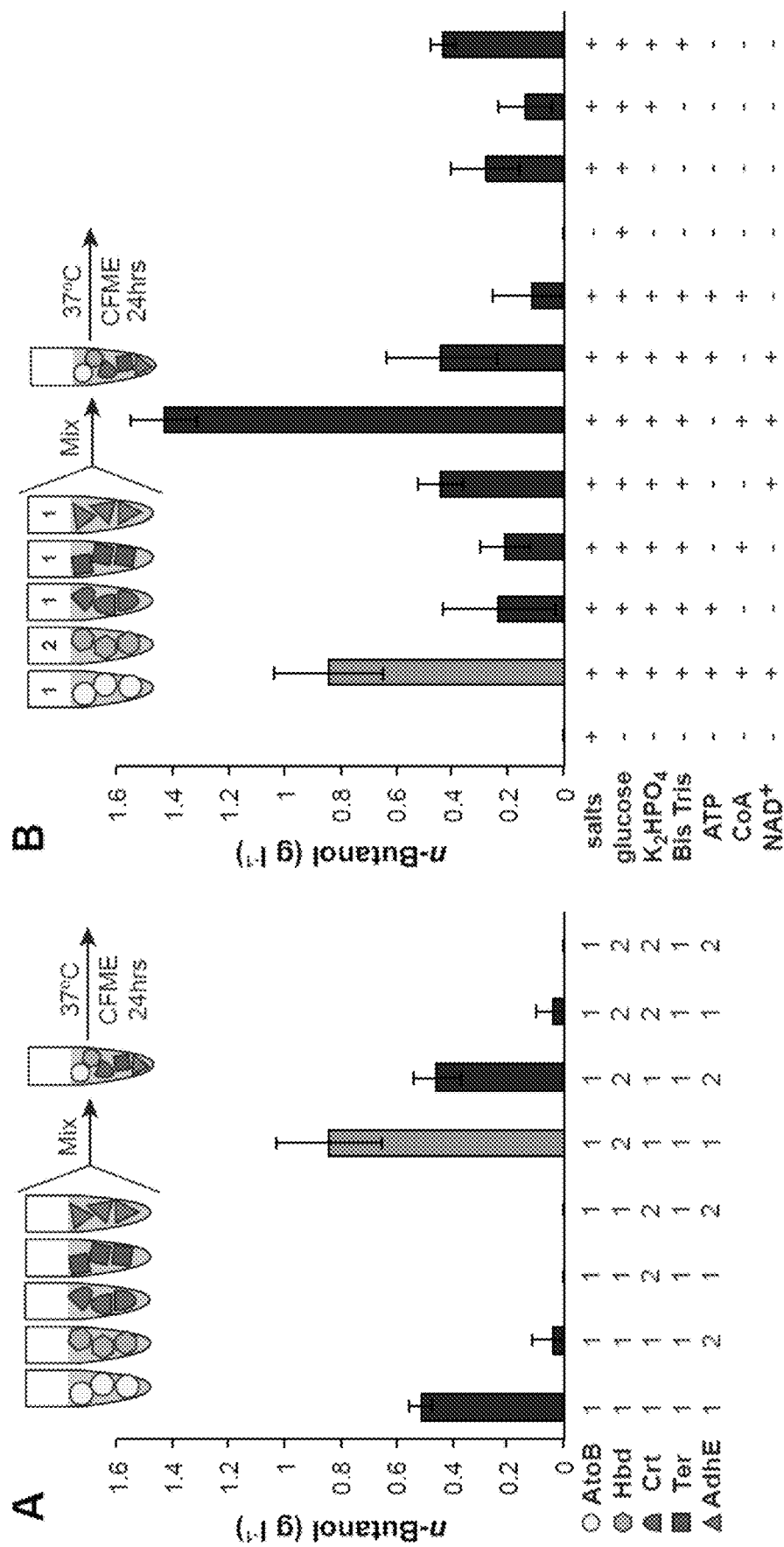
FIG. 3. Enzyme and physiochemical optimizations lead to increased yields of CFME n-butanol production. (A) Reactions for n-butanol production from glucose were performed using different sets of five crude lysates mixed together to obtain unique combinations of selectively overexpressed enzymes with AtoB, Hbd, Crt, Ter, and AdhE activities. Lysate mixes were combined with glutamate salts ($Mg^+$, $NH_4^+$, $K^+$), phosphate ($K_2HPO_4$), buffer (Bis Tris), and cofactors (ATP, CoA, $NAD^+$) and incubated for 24 h at 37° C. (B) To enhance yields and optimize pathway performance, a physiochemical optimization was performed with or without glutamate salts ($Mg^+$, $NH_4^+$, $K^+$), phosphate ($K_2HPO_4$), buffer (Bis Tris), and cofactors (ATP, CoA, $NAD^+$)) of cell-free reactions producing n-butanol. Reactions incubated for 24 h at 37° C. The grey bars represent the same recipe in (A) and in (B). All error bars represent standard deviations with $n \geq 3$ independent reactions.

Following demonstration of activating n-butanol synthesis, we next aimed to modularly build n-butanol synthesis pathways with different enzyme homologs to improve pathway performance. We cycled through multiple distinct ensembles of enzymes by mixing and matching lysates containing different versions of enzymes necessary to complete the biosynthetic n-butanol pathway. Trying out different homologs in this manner allowed us to quickly identify a better set of enzymes producing n-butanol at 0.84±0.19 g l$^{-1}$ (0.09 mol n-butanol/mol glucose) (FIG. 3A). Specifically, we showed that Hbd2 from C. beijerinckii enabled a 65% increase in n-butanol synthesis titers over Hbd1 from C. acetobutylicum. A follow-up experiment doubling the Hbd1 enzyme did not alter the amount of n-butanol produced, suggesting that this increase was not due to discrepancies in enzyme concentrations in the lysate (FIG. 8). However, further studies of these enzymes would elucidate whether the observed n-butanol production was a result of using BL21(DE3) extract without heterologous genes expressed (used for normalization), which may have more active glycolytic and byproduct pathways that could divert flux away from n-butanol.

While the selection of enzymes is crucial to improving n-butanol production, the value of each physiochemical parameter of the cell-free system also affects n-butanol production and becomes key in further optimization and debugging of the pathway. To demonstrate the facile nature of combinatorial optimizations in our cell-free framework, we explored changes in the ionic composition because the composition of salts added to in vitro systems affects the systems' performance[46,47,49,50]. Specifically, we tested the effect of using glutamate, acetate, and chloride salts on n-butanol production and found that glutamate salts perform more than 15% better than the other salt compositions (FIG. 9). Our results are consistent with previous works, which have shown that glutamate salts better mimic the intracellular cytoplasmic conditions of *E. coli* to co-activate authentic biological processes such as the in vitro co-activation of central metabolism, oxidative phosphorylation, and protein synthesis[46].

Beyond studying pathway performance by altering the ionic composition, the states of critical cofactors (organic molecules necessary for enzyme catalysis) can also be studied. The balance of cofactors, such as oxidized and reduced NAD, is critical to energy regeneration within the lysate by also the heterologous pathway under investigation. In our cell-free framework, the lack of a cell wall enables direct sample acquisition, reaction monitoring, and control. We used this flexibility to study the impact of the ratio of initial cofactors in the reaction to see the ratio's effect on n-butanol production. We found that the ratio of NAD(H) at the start of the reaction (e.g., NAD:NADH: 1:0, 1:0.5, 1:1, 0.5:1, 0:1), keeping the total cofactor concentration at 0.5 mM, plays a minimal role in how much n-butanol can be produced (FIG. 10). This suggests that metabolism in the lysate may control the overall levels of reduced and oxidized cofactor, which is consistent with data from Kay and Jewett[36].

Understanding that some components play more of a role in pathway performance than others, we next performed a number of reactions to identify which added components are necessary for n-butanol production with a particular interest in the three added cofactors (ATP, NAD, and CoA). The supplementation of cofactors to cell-free reactions would be costly and hinder industrial practicality of this technology if it were proposed as a biomanufacturing platform. In our study of cell-free systems as a prototyping framework, we surprisingly found that omitting ATP boosts n-butanol production by greater than 180% from $0.84 \pm 0.19$ g $l^{-1}$ to $1.43 \pm 0.12$ g $l^{-1}$ (0.11 mol n-butanol/mol glucose) (FIG. 3B). More unexpectedly, by just adding salts to mimic the cytoplasm and glucose as a starting substrate we are able to produce n-butanol at $0.28 \pm 0.12$ g $l^{-1}$. In other words, if lysates are prepared without dialysis, as we have done, cofactors remaining in the lysate are sufficient for the cell-free transformation and do not need to be added. Collectively, our results here show that the cell-free framework offers a strategy to explore how enzyme variants, substrates, cofactors, ionic composition, etc. can be varied in unique combinations to influence pathway performance. While CFME (i.e., selective enriching or functionalizing the lysate with pathway enzymes prior to extract generation) provides us with a rather quick way to screen enzyme ensembles and reaction conditions, this approach is limited by the cell's ability to produce the enzymes individually in vivo, a limitation that we address below.

3.2 Cell-Free Protein Synthesis Driven Metabolic Engineering.

Figure 4:
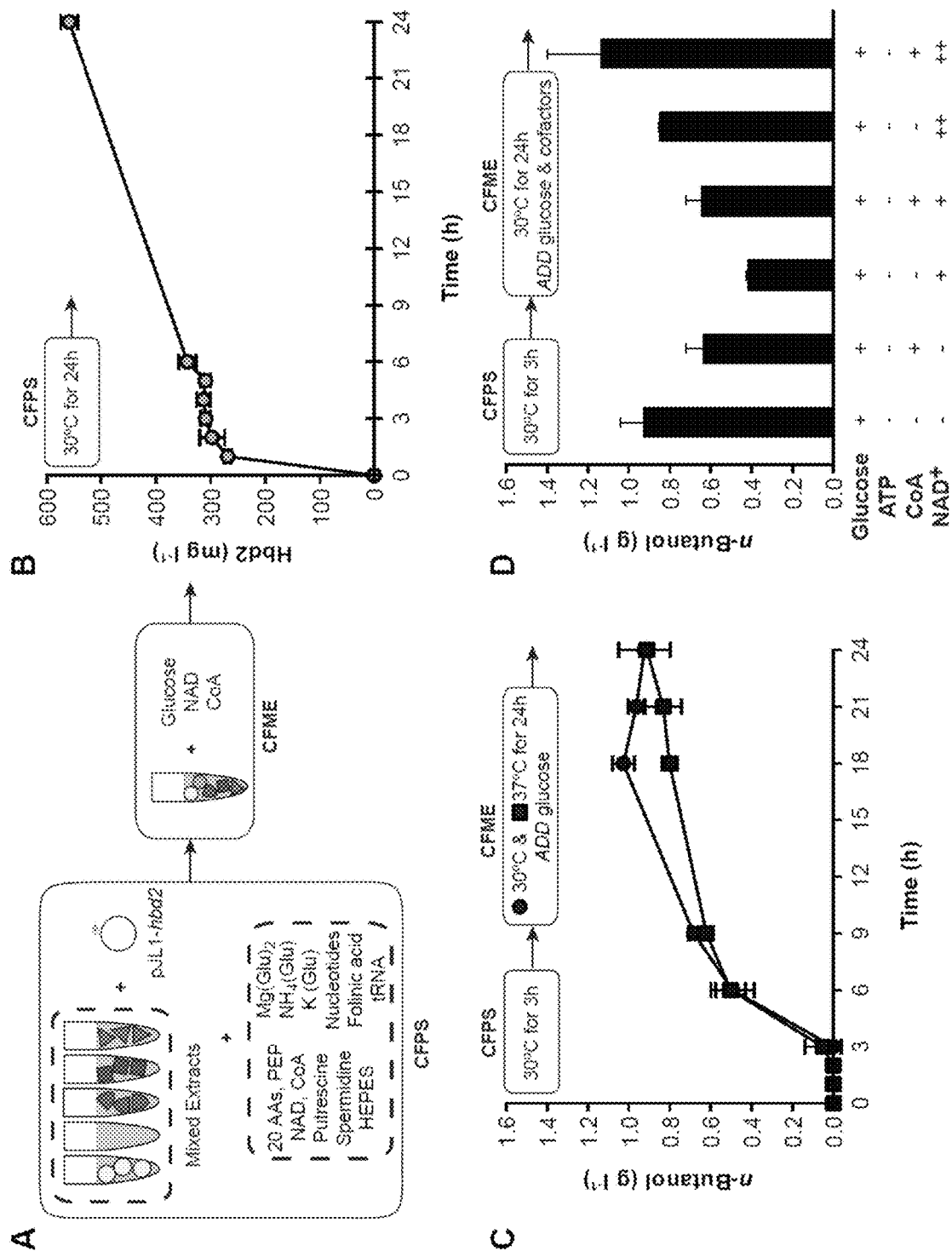
FIG. 4. Cell-free protein synthesis of entry enzyme activates n-butanol production in vitro by CFPS-ME approach. (A) Diagram describing the CFPS-ME experimental design. (B) Cell-free protein synthesis titers of Hbd2 from pJL1-hbd2 in a crude lysate mixture containing AtoB (EC), Crt1 (CA), Ter1 (TD), and AdhE1 (CA) overexpressed as determined by radioactive $^{14}C$-leucine incorporation. CFPS reactions incubated over a 24-hr period at 30° C. (C) n-butanol production in the same mixed lysate system activated by cell-free protein synthesis of Hbd2 run at 30° C. for 3 h. Glucose was added to activate the n-butanol pathway and CFME reactions were incubated over a 24-hr period at both 30° C. and 37° C. (D) Cofactor (ATP, CoA, $NAD^+$) optimization of downstream (ME portion of the CFPS-ME approach) cell-free reactions producing n-butanol were performed. Minus (−) signs represent no cofactor added, plus (+) signs represent mM amounts of cofactor to match conditions in CFME-alone experiments, and plus-plus (++) reactions represent double the amount of that cofactor. Reactions incubated for 24 h at 30° C. All error bars represent standard deviations with $n \geq 3$ independent reactions.

We next aimed to combine CFPS and CFME to modularly build the n-butanol pathway for forward engineering. This is dissimilar from previous works in which synthetic in vitro pathways have been built by purified enzymes or using lysates selectively enriched by heterologously expressed enzymes. Integration of CFPS enables one to speed up DBT cycle time for prospecting biosynthetic pathways. Indeed, using CFPS to express enzymes can reduce the time to build pathways to hours rather than days. As a proof-of-concept of this approach, we tested making Hbd2 (the non-native entry enzyme to the pathway) by CFPS to activate n-butanol production (FIG. 4A). The key idea of the experiment was that the pathway would remain inactive (as downstream enzymes will not have their substrates) until active Hbd2 was synthesized. We chose to validate CFPS-ME in a three-step process. First, we quantified our ability to express Hbd2 in a CFPS reaction comprised of a mixture of lysates harboring selectively enriched pathway enzymes lacking Hbd2. This was important because typical CFPS systems use lysates from cells harvested in mid-late exponential phase, where as our lysates were collected 4 h post-induction of pathway enzymes. Second, we studied the ability to activate the entire pathway by combining CFPS and CFME. Third, we carried out a series of optimizations to try to increase yields.

For CFPS, we used the tunable and well characterized PANOx-SP CFPS system developed by Jewett and Swartz[47] to quantitatively test the synthesis of Hbd2. CFPS reactions at 30° C. were allowed to run for 24 h in batch operation and the yields of cell-free synthesized Hbd2 was quantified by monitoring $^{14}$C-leucine incorporation. We based the system on a mixture of lysates used above, except the lysate with Hbd2 was not included. Endogenous protein synthesis machinery should act to synthesize and fold desired protein products upon incubation with essential substrates (e.g., amino acids, nucleotides, DNA or mRNA, energy substrates, cofactors, and salts). In this case, we showed that when the DNA for the Hbd2 enzyme on a pJL1 vector was added, the mixed extract could produce $559 \pm 15$ mg $l^-$ of Hbd2 over a 24-hour period (FIG. 4B). Based on this result and the fact that this reaction was over 50% complete by three hours, we chose to run all subsequent CFPS reactions for three hours, which should provide sufficient protein quantities for prototyping.

We next investigated the ability of the cell-free synthesized Hbd2 to activate the full n-butanol pathway. After three hours of CFPS, we initiated n-butanol metabolism by adding 200 mM glucose to the reactions. We showed that CFPS of Hbd2 could activate n-butanol metabolism reaching a titer of $0.92 \pm 0.13$ g $l^{-1}$ (FIG. 4C). Negative control reactions without synthesis of the Hbd2 did not produce n-butanol. Notably, the CFME portion resulted in the same n-butanol yields when carried out at either 30 or 37° C., so for ease we selected 30° C. for all future experiments to have the CFPS and CFME portions performed at the same temperature. As in the CFME system alone, we found that small molecules, cofactors, etc. can modulate pathway performance. For example, we found that adding both NAD and CoA with glucose to initiate n-butanol metabolism after CFPS gave us $1.22 \pm 0.22$ g $l^{-1}$ n-butanol (FIG. 4D). Collectively, our results prove for the first time to our knowledge the ability to combine CFPS and CFME to support a highly active biosynthetic pathway.

Figure 5:
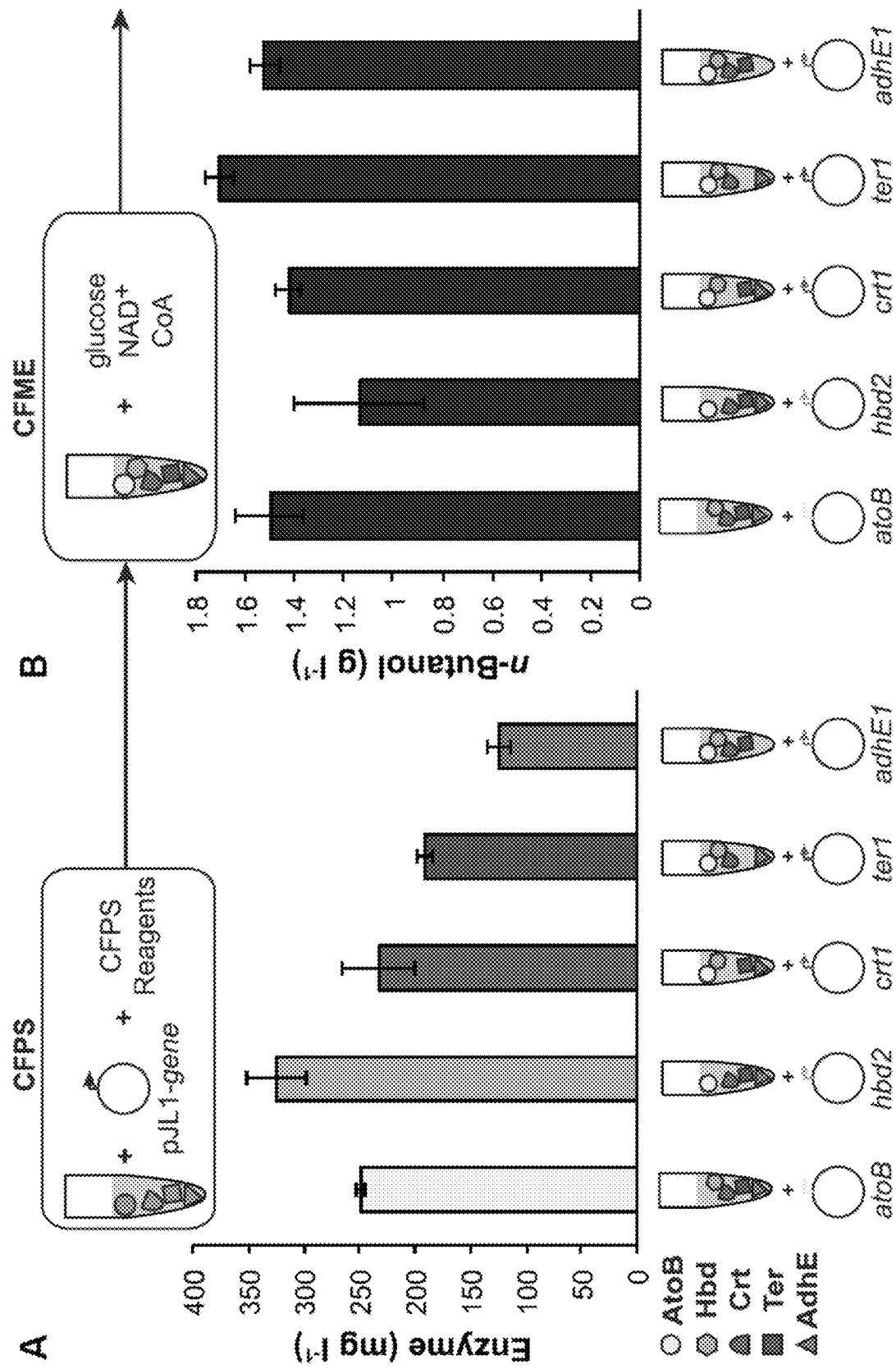
FIG. 5. Using cell-free protein synthesis to activate metabolism from any node in the biosynthetic pathway. (a) Cell-free protein synthesis titers of AtoB (EC), Hbd2 (CB), Crt1 (CA), Ter1 (CA), and AdhE1 (CA) off pJL1 constructs in separate reaction mixtures as determined by radioactive $^{14}C$-leucine incorporation. Each reaction mixture contained crude lysates with all pathway enzymes except the one made by CFPS. CFPS reactions were incubated for 3 h at 30° C. (b) n-butanol production in the same mixed lysate system activated by CFPS of each enzyme run at 30° C. for 3 h.
Figure 5:
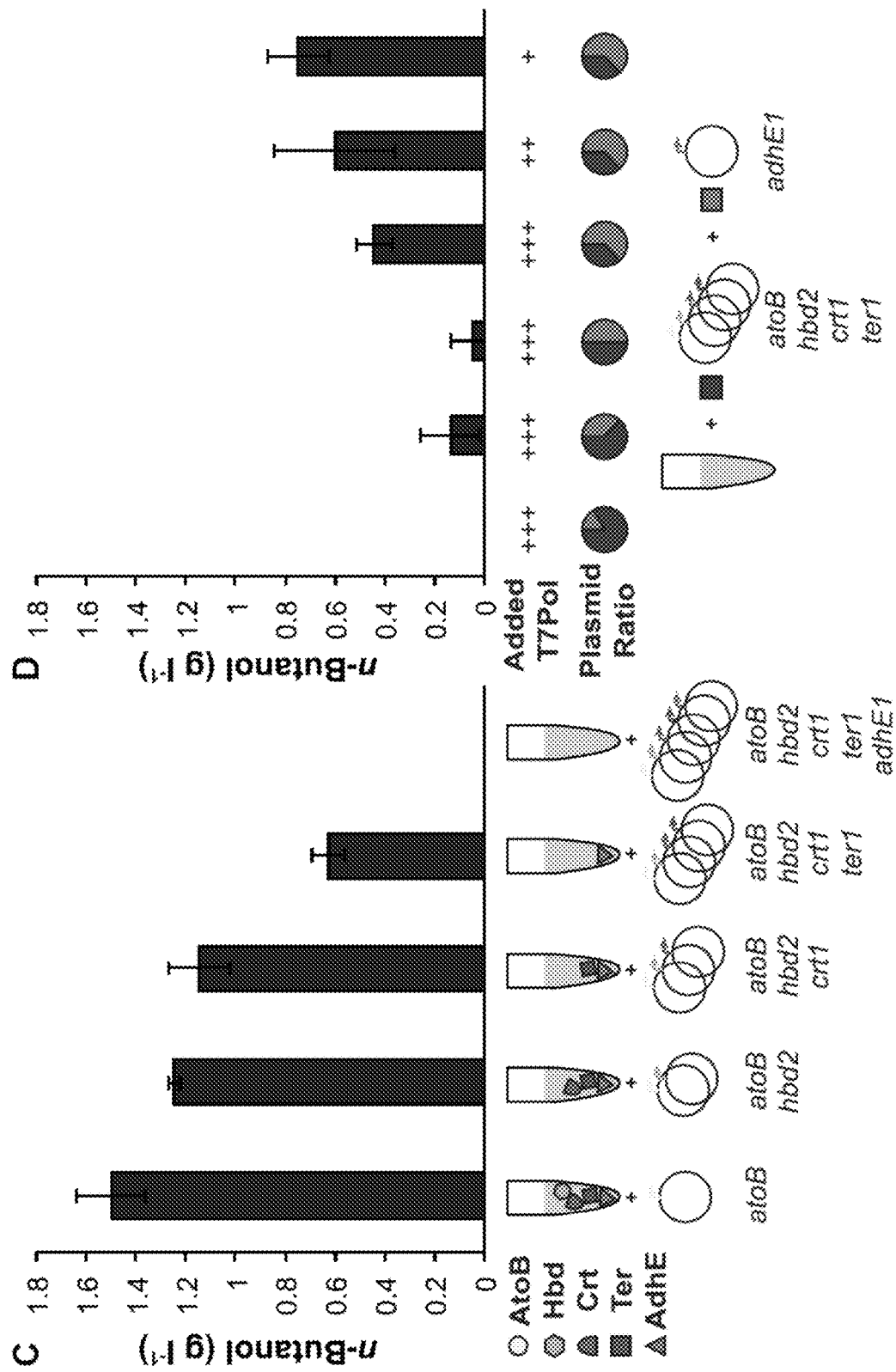

We further extended this proof-of-concept to activate n-butanol production using CFPS at any pathway node by producing each n-butanol pathway enzyme. Using mixed extracts with all but one necessary enzyme, we performed CFPS of the 'missing enzyme' and saw that each enzyme could be produced individually at more than 100 mg $l^{-1}$ without optimization (FIG. 5A). We then proved that full product of each protein is made exclusively in each reaction by an autoradiogram (FIG. 11). After validating expression of each enzyme, we then performed CFPS-ME reactions. We carried out three-hour CFPS reactions and then initiated the n-butanol pathway by adding glucose, NAD, and CoA, because supplementation of CFPS-ME reactions with both NAD and CoA increased n-butanol titers for Hbd2 (FIG. 4D). Strikingly, CFPS-ME could be used for each of the pathway enzymes to produce n-butanol at levels as high as $1.71 \pm 0.06$ g $l^{-1}$ (FIG. 5B).

We next set out to demonstrate we could build the entire pathway by CFPS of the pathway enzymes in our extracts. To this end, we extended the number of enzymes made in vitro one by one, by adding equal amounts of DNA of each, and saw that when we made one, two, three, and four of the five enzymes necessary in vitro we could produce n-butanol at levels between ~0.6 and ~1.4 g l⁻ (FIG. 5C). Again, full-length product of each protein is made in each reaction as shown by autoradiogram (FIG. 12). However, as we increase the number of enzymes produced by CFPS, the amount of n-butanol synthesized decreases. In fact, when we tried to produce all five enzymes in vitro we were initially unable to make any n-butanol. We attribute this drop in n-butanol production to there not being enough of the last enzyme in the pathway, AdhE, seen by quantification of the enzymes produced by CFPS (FIG. 13). However, we were able to make all enzymes in vitro at sufficient levels necessary to make n-butanol at $0.75\pm0.12$ g $l^{-1}$ by increasing the plasmid DNA encoding AdhE to more than 50% of the total DNA added, (FIG. 5D; FIG. 14). Reduced T7 polymerase added shows improvements in n-butanol production. Typical CFPS systems supplement T7 polymerase stored in glycerol, and increasing glycerol concentrations can be deleterious to the CFPS system. The extract used in this study contains T7 polymerase expressed in vivo prior to extract preparation, so T7 polymerase in the extract is expected to be sufficient without supplementation. Based on our result that added ATP was deleterious to n-butanol production by CFME (FIG. 3B), the ATP used in CFPS might be expected to inhibit CFPS-ME n-butanol titers if ATP is long-lived. We have previously shown that ATP concentrations are stable around 200 μM over a ~6-8 hour batch CFPS reaction[47]. Though, a negative effect from ATP is expected, it is difficult to use the CFME optimization conditions for CFPS-ME, given the added complexity of protein synthesis. Our results importantly showed that we could build a five-step heterologous pathway to make n-butanol in vitro in three hours.

3.3 Rapid Prototyping and Enzyme Discovery with CFPS-ME.

The ability to use CFPS-ME to produce enzymes for n-butanol biosynthesis allows us to test pathway enzymes without expressing enzymes in the host cell. As a model case study, we decided to test for improved pathway performance (increased n-butanol production) by swapping out some of our initial Ter and AdhE enzymes for a variety of homologs. In less than a day, we studied 4 Ter and 3 AdhE homologs in a combined CFPS-ME reaction. In all cases, we observed synthesis of n-butanol, though lower than our previous best-performing enzymes (FIG. 6A). Five of these variants come from species never tested before.

Having demonstrated the ability to explore enzyme homologs using CFPS-ME, we then set out to demonstrate the potential for using linear DNA templates instead of plasmids. Using linear DNA molecules, i.e. PCR products, would expedite the process since the entire process could be done without cells and we could avoid laborious cloning steps. As a model system, we first repeated the experiments presented in FIG. 6 with linear templates and observed that the linear DNA templates can successfully be expressed to complete the n-butanol biosynthesis pathway (FIG. 15). Next, we chose to screen multifunctional enzymes that to our knowledge have never before used for n-butanol production. We selected four enzymes with proposed Hbd and Crt functionalities that were identified by NCBI-BLAST searches. By preparing reactions with three different enzyme mixtures (mixed extracts with overexpressed enzymes prior to lysis) (1) without Hbd, (2) without Crt, and (3) without Hbd and Crt, we could characterize each enzyme variant by their ability to perform each enzymatic function. We discovered that each of these enzymes could activate n-butanol synthesis, and the proposed Hbdcrt6 from *Sulfolobus acidocaldarius* only had Hbd functionality (FIG. 6B). The ability to use linear DNA templates for CFPS-ME makes possible the ability to rapidly screen individual and sets of enzymes completely in vitro. Here, we used this approach to parse out individual functionalities of multi-functional enzymes.

Discussion

In this study, we developed a new cell-free framework for prototyping biosynthetic pathways and screening enzymes. In one scenario, we overexpress individual pathway components in cells, lyse these cells, and mix and match lysates in cell-free cocktails to study biochemical pathway performance. In a distinct thrust from typical in vitro systems, our approach allows us to study heterologous pathways in the context of native metabolism. In another scenario, we bypass in vivo expression altogether by using CFPS to enrich lysates with different enzymes for combinatorial assembly of different pathways. The combination of CFPS to express homologs of individual biosynthetic enzymes for studying pathway performance is also a distinction of our workflow. In addition, the use of linear PCR templates, which could be improved by DNA stability techniques (e.g., the addition of purified GamS protein)[30], allows us to avoid in vivo cloning steps altogether. Our CFPS-ME approach should therefore be faster than conventional approaches to select enzymes and pathway designs in cells (hours instead of days/weeks), and enables parallelized pathway construction of combinatorial designs to accelerate DBT cycles.

A key conceptual innovation of our work is that the DBT unit can be cell-free lysates rather than genetic constructs. Engineering large biosynthetic systems composed of many genes in microbes remains challenging[27]. One of the many obstacles is simply how many different genetic designs with beneficial chances are feasible to make. Cell-free systems have already been shown to screen genetic designs to improve enzyme performance at a rapid rate[51]. Our CFPS-ME framework should allow researchers to study more designs than previously possible by rapidly prototyping enzyme performance in vitro before putting designs into a host. As an example, a six-step biosynthetic pathway testing 5 homologs for each enzymatic step would require testing of 15,625 pathway combinations. While this set of combinations exceeds typical pipelines pursued in cells today, our CFPS-ME system could leverage robotic or automated liquid-handling systems to access such design space.

The goal of this manuscript was to provide a new approach to building biosynthetic pathways in a modular fashion in vitro. Now achieved, we plan to optimize a large-scale fermentation process with the CFPS-ME approach in the future. Towards this goal, we additionally carried out experiments to show that protein expression in the cell-free system translates to the in vivo system. Specifically, we took all Ter homologs screened in vitro by CFPS-ME (FIG. 6) and expressed them in whole cells in vivo. All but one of the Ter homolog proteins can be expressed in cells on a first pass (as determined by SDS-page expression, FIG. 16). These data show that protein expression in the cell-free system can translate to the in vivo system. Thus our approach holds promise for identifying good enzymes that can be expressed in cells, following a body of work that uses in vitro enzyme assays to identify enzymes with the best-performing biochemical characteristics for desired metabolic transformations prior to putting them into a host. For example, Liao and colleagues showed that in vitro reconstitution could be used to construct the non-oxidative glycolytic pathway prior to in vivo expression[52], and Zhu et al. reconstituted the mevalonate pathway in vitro to study pathway kinetics before using the pathway in vivo for the production of farnesene[53].

Our cell-free approach mimics the intracellular environment of *E. coli*, where endogenous glycolytic enzymes from the cell extract convert glucose to AcCoA. Thus, our platform enables many different biosynthetic pathways to be studied in the context of central metabolism with enhanced control inherent to in vitro systems. Here, we were able to increase n-butanol production by ~200% of our initial starting conditions (up to ~1.5 g l$^{-1}$) by simply testing the performance of different enzymes sets and adjusting the physicochemical environment. While it is be difficult to compare in a normalized fashion the in vitro process to the in vivo process, our results (given as final measured concentration) are higher than some published reports of n-butanol production in comparable genomically unmodified hosts (FIG. 17)[37,54-56]. However, Bond-Watts et al. notably reported titers of 4.6 g l$^{-1}$ in a genomically unmodified host by selecting a particular set of synergistic enzymes and taking advantage of their chemistries[18]. Given the reasonable yields, we were curious as to how the CFPS-ME reactions would perform at increased scale. We thus performed additional experiments of increasing size reactions to give confidence in our quantitative yields. Specifically, the reaction volume of CFPS-ME reactions was scaled from 25 to 250 μL, an order of magnitude increase (FIG. 18). Our data shows that these reactions are scalable and are consistent with several previous works showing the ability of cell-free systems to scale linearly[36,57-60].

Looking forward, specialty chemicals, natural products, and materials offer an extremely diverse set of compounds with a seemingly infinite set of structures and bioactivities. For example, we have applied our approach to reconstruct nonribosomal peptide biosynthesis directly from DNA (FIG. 19). Specifically, we utilized the proteins involved in the first steps of gramicidin S biogenesis as a model to show the potential for making and prospecting natural products with our approach (FIGS. 20 and 21). Our CFPS-ME approach offers a new discovery pipeline to leverage advances in DNA sequencing and DNA synthesis to optimize biosynthetic pathways, discover new enzymes, and test new hypotheses. Because it is an open system, cell-free reactors can be readily interrogated for intermediate product formation, such as by the online, high speed LC/MS approaches used by Panke and colleagues for optimization of glycolysis in cell-free extracts. Cell-free systems in tandem with high-end metabolomics could offer a high degree of flexibility to model the kinetics and stability of individual enzymes, measure metabolite fluxes in multistep pathways, and experimentally isolate many other parameters confounded in living organisms. This has potential to speed up metabolic engineering DBT cycles.

REFERENCES

1. Bornscheuer, U. T. et al. Engineering the third wave of biocatalysis. Nature 485, 185-194, doi:10.1038/nature11117 (2012).
2. Fritz, B. R., Timmerman, L. E., Daringer, N. M., Leonard, J. N. & Jewett, M. C. Biology by design: from top to bottom and back. Journal of biomedicine & biotechnology 2010, 232016, doi:10.1155/2010/232016 (2010).
3. Curran, K. A. & Alper, H. S. Expanding the chemical palate of cells by combining systems biology and metabolic engineering. Metabolic engineering 14, 289-297, doi:10.1016/j.ymben.2012.04.006 (2012).
4. Rollié, S., Mangold, M. & Sundmacher, K. Designing biological systems: Systems Engineering meets Synthetic Biology. Chemical Engineering Science 69, 1-29, doi: 10.1016/j.ces.2011.10.068 (2012).
5. Erickson, B., Nelson & Winters, P. Perspective on opportunities in industrial biotechnology in renewable chemicals. Biotechnology journal 7, 176-185, doi:10.1002/biot.201100069 (2012).
6. Nielsen, J. et al. Engineering synergy in biotechnology. Nature chemical biology 10, 319-322, doi:10.1038/nchembio.1519 (2014).
7. Demain, A. L. Importance of microbial natural products and the need to revitalize their discovery. Journal of industrial microbiology & biotechnology 41, 185-201, doi:10.1007/s10295-013-1325-z (2014).
8. Harvey, A. L., Edrada-Ebel, R. & Quinn, R. J. The re-emergence of natural products for drug discovery in the genomics era. Nature reviews. Drug discovery 14, 111-129, doi:10.1038/nrd4510 (2015).
9. Kern, A., Tilley, E., Hunter, I. S., Legisa, M. & Glieder, A. Engineering primary metabolic pathways of industrial micro-organisms. Journal of biotechnology 129, 6-29, doi:10.1016/j.jbiotec.2006.11.021 (2007).
10. Nielsen, J. Metabolic engineering. Applied Microbiology and Biotechnology 55, 263-283, doi:10.1007/s002530000511 (2001).
11. Hodgman, C. E. & Jewett, M. C. Cell-free synthetic biology: thinking outside the cell. Metabolic engineering 14, 261-269, doi:10.1016/j.ymben.2011.09.002 (2012).
12. Kwok, R. Five hard truths for synthetic biology. Nature 463, 288-290, doi: 10.1038/463288a (2010).
13. Green, E. M. Fermentative production of butanol—the industrial perspective. Current opinion in biotechnology 22, 337-343, doi:10.1016/j.copbio.2011.02.004 (2011).
14. Lutke-Eversloh, T. & Bahl, H. Metabolic engineering of *Clostridium acetobutylicum*: recent advances to improve butanol production. Current opinion in biotechnology 22, 634-647, doi:10.1016/j.copbio.2011.01.011 (2011).
15. Atsumi, S. et al. Metabolic engineering of *Escherichia coli* for 1-butanol production. Metabolic engineering 10, 305-311, doi:10.1016/j.ymben.2007.08.003 (2008).
16. Steen, E. J. et al. Metabolic engineering of *Saccharomyces cerevisiae* for the production of n-butanol. Microbial cell factories 7, 36, doi: 10.1186/1475-2859-7-36 (2008).
17. Shen, C. R. et al. Driving forces enable high-titer anaerobic 1-butanol synthesis in *Escherichia coli*. Applied and environmental microbiology 77, 2905-2915, doi:10.1128/AEM.03034-10 (2011).
18. Bond-Watts, B. B., Bellerose, R. J. & Chang, M. C. Enzyme mechanism as a kinetic control element for designing synthetic biofuel pathways. Nature chemical biology 7, 222-227, doi:10.1038/nchembio.537 (2011).
19. Dong, H. et al. Engineering *Escherichia coli* Cell Factories for n-Butanol Production. Advances in biochemical engineering/biotechnology, doi:10.1007/10_2015_306 (2015).
20. Keasling, J. D. Manufacturing molecules through metabolic engineering. Science 330, 1355-1358, doi:10.1126/science.1193990 (2010).
21 Keasling, J. D. Synthetic biology and the development of tools for metabolic engineering. Metabolic engineering 14, 189-195, doi:10.1016/j.ymben.2012.01.004 (2012).

22. Jensen, M. K. & Keasling, J. D. Recent applications of synthetic biology tools for yeast metabolic engineering. FEMS Yeast Res, doi:10.1111/1567-1364.12185 (2014).
23. Dai, Z. & Nielsen, J. Advancing metabolic engineering through systems biology of industrial microorganisms. Current opinion in biotechnology 36, 8-15, doi:10.1016/j.copbio.2015.08.006 (2015).
24. Lee, S. Y. & Kim, H. U. Systems strategies for developing industrial microbial strains. Nat Biotechnol 33, 1061-1072, doi:10.1038/nbt.3365 (2015).
25. Lee, J. W. et al. Systems metabolic engineering of microorganisms for natural and non-natural chemicals. Nature chemical biology 8, 536-546, doi:10.1038/nchembio.970 (2012).
26. Yadav, V. G., De Mey, M., Giaw Lim, C., Kumaran Ajikumar, P. & Stephanopoulos, G. The future of metabolic engineering and synthetic biology: Towards a systematic practice. Metabolic engineering 14, 233-241, doi:10.1016/j.ymben.2012.02.001 (2012).
27. Smanski, M. J. et al. Functional optimization of gene clusters by combinatorial design and assembly. Nat Biotechnol 32, 1241-1249, doi:10.1038/nbt.3063 (2014).
28. Boyle, P. M. & Silver, P. A. Parts plus pipes: synthetic biology approaches to metabolic engineering. Metabolic engineering 14, 223-232, doi:10.1016/j.ymben.2011.10.003 (2012).
29. Carlson, E. D., Gan, R., Hodgman, C. E. & Jewett, M. C. Cell-free protein synthesis: applications come of age. Biotechnology advances 30, 1185-1194, doi:10.1016/j.biotechadv.2011.09.016 (2012).
30. Sun, Z. Z., Yeung, E., Hayes, C. A., Noireaux, V. & Murray, R. M. Linear DNA for rapid prototyping of synthetic biological circuits in an *Escherichia coli* based TX-TL cell-free system. ACS synthetic biology 3, 387-397, doi:10.1021/sb400131a (2014).
31. Siegal-Gaskins, D., Tuza, Z. A., Kim, J., Noireaux, V. & Murray, R. M. Gene circuit performance characterization and resource usage in a cell-free "breadboard". ACS synthetic biology 3, 416-425, doi:10.1021/sb400203p (2014).
32. Dudley, Q. M., Karim, A. S. & Jewett, M. C. Cell-free metabolic engineering: biomanufacturing beyond the cell. Biotechnology journal 10, 69-82, doi:10.1002/biot.201400330 (2015).
33. Zhang, Y. H. Production of biofuels and biochemicals by in vitro synthetic biosystems: Opportunities and challenges. Biotechnology advances 33, 1467-1483, doi:10.1016/j.biotechadv.2014.10.009 (2015).
34. You, C. & Zhang, Y. H. Cell-free biosystems for biomanufacturing. Advances in biochemical engineering/biotechnology 131, 89-119, doi:10.1007/10_2012_159 (2013).
35. Guterl, J. K. et al. Cell-free metabolic engineering: production of chemicals by minimized reaction cascades. ChemSusChem 5, 2165-2172, doi:10.1002/cssc.201200365 (2012).
36. Kay, J. E. & Jewett, M. C. Lysate of engineered *Escherichia coli* supports high-level conversion of glucose to 2,3-butanediol. Metabolic engineering 32, 133-142, doi:10.1016/j.ymben.2015.09.015 (2015).
37. Krutsakorn, B. et al. In vitro production of n-butanol from glucose. Metabolic engineering 20, 84-91, doi:10.1016/j.ymben.2013.09.006 (2013).
38. Ninh, P. H., Honda, K., Sakai, T., Okano, K. & Ohtake, H. Assembly and multiple gene expression of thermophilic enzymes in *Escherichia coli* for in vitro metabolic engineering. Biotechnol Bioeng 112, 189-196, doi:10.1002/bit.25338 (2015).
39. Welch, P. & Scopes, R. K. Studies on cell-free metabolism: Ethanol production by a yeast glycolytic system reconstituted from purified enzymes. Journal of biotechnology 2, 257-273, doi:10.1016/0168-1656(85)90029-x (1985).
40. Swartz, J. R. Transforming biochemical engineering with cell-free biology. AIChE Journal 58, 5-13, doi:10.1002/aic.13701 (2012).
41. Dodevski, I., Markou, G. C. & Sarkar, C. A. Conceptual and methodological advances in cell-free directed evolution. Curr Opin Struct Biol 33, 1-7, doi:10.1016/j.sbi.2015.04.008 (2015).
42. Henrich, E., Hein, C., Dotsch, V. & Bernhard, F. Membrane protein production in *Escherichia coli* cell-free lysates. FEBS Lett 589, 1713-1722, doi:10.1016/j.febslet.2015.04.045 (2015).
43. Zemella, A., Thoring, L., Hoffmeister, C. & Kubick, S. Cell-Free Protein Synthesis: Pros and Cons of Prokaryotic and Eukaryotic Systems. Chembiochem 16, 2420-2431, doi:10.1002/cbic.201500340 (2015).
44. Noireaux, V., Bar-Ziv, R. & Libchaber, A. Principles of cell-free genetic circuit assembly. Proc Natl Acad Sci USA 100, 12672-12677, doi:10.1073/pnas.2135496100 (2003).
45. Goshima, N. et al. Human protein factory for converting the transcriptome into an in vitro-expressed proteome. Nature Methods 5, 1011-1017, doi:10.1038/nmeth.1273 (2008).
46. Jewett, M. C., Calhoun, K. A., Voloshin, A., Wuu, J. J. & Swartz, J. R. An integrated cell-free metabolic platform for protein production and synthetic biology. Mol Syst Biol 4, 220, doi:10.1038/msb.2008.57 (2008).
47. Jewett, M. C. & Swartz, J. R. Mimicking the *Escherichia coli* cytoplasmic environment activates long-lived and efficient cell-free protein synthesis. Biotechnol Bioeng 86, 19-26, doi:10.1002/bit.20026 (2004).
48. Korman, T. P. et al. A synthetic biochemistry system for the in vitro production of isoprene from glycolysis intermediates. Protein Sci 23, 576-585, doi:10.1002/pro.2436 (2014).
49. Record, M. T., Courtenay, E. S., Cayley, S. & Guttman, H. J. Biophysical compensation mechanisms buffering *E. coli* protein-nucleic acid interactions against changing environments. Trends in Biochemical Sciences 23, 190-194, doi:10.1016/s0968-0004(98)01207-9 (1998).
50. Jewett, M. C., Fritz, B. R., Timmerman, L. E. & Church, G. M. In vitro integration of ribosomal RNA synthesis, ribosome assembly, and translation. Mol Syst Biol 9, 678, doi:10.1038/msb.2013.31 (2013).
51. Daugherty, A. B., Govindarajan, S. & Lutz, S. Improved biocatalysts from a synthetic circular permutation library of the flavin-dependent oxidoreductase old yellow enzyme. J Am Chem Soc 135, 14425-14432, doi:10.1021/ja4074886 (2013).
52. Bogorad, I. W., Lin, T. S. & Liao, J. C. Synthetic non-oxidative glycolysis enables complete carbon conservation. Nature 502, 693-697, doi:10.1038/nature12575 (2013).
53. Zhu, F. et al. In vitro reconstitution of mevalonate pathway and targeted engineering of farnesene overproduction in *Escherichia coli*. Biotechnol Bioeng 111, 1396-1405, doi: 10.1002/bit.25198 (2014).
54. Gulevich, A. Y., Skorokhodova, A. Y., Sukhozhenko, A. V., Shakulov, R. S. & Debabov, V. G. Metabolic engi- 55. Nielsen, D. R. et al. Engineering alternative butanol production platforms in heterologous bacteria. Metabolic engineering 11, 262-273, doi:10.1016/j.ymben.2009.05.003 (2009).
56. Inui, M. et al. Expression of *Clostridium acetobutylicum* butanol synthetic genes in *Escherichia coli*. Appl Microbiol Biotechnol 77, 1305-1316, doi:10.1007/s00253-007-1257-5 (2008).
57. Yin, G. et al. A glycosylated antibodies and antibody fragments produced in a scalable in vitro transcription-translation system. MAbs 4, 217-225, doi:10.4161/mabs.4.2.19202 (2012).
58. Zawada, J. F. et al. Microscale to manufacturing scale-up of cell-free cytokine production—a new approach for shortening protein production development timelines. Biotechnol Bioeng 108, 1570-1578, doi:10.1002/bit.23103 (2011).
59. Voloshin, A. M. & Swartz, J. R. Efficient and scalable method for scaling up cell free protein synthesis in batch mode. Biotechnol Bioeng 91, 516-521, doi:10.1002/bit.20528 (2005).
60. Hong, S. H. et al. Improving cell-free protein synthesis through genome engineering of *Escherichia coli* lacking release factor 1. Chembiochem 16, 844-853, doi:10.1002/cbic.201402708 (2015).
61. Bujara, M., Schumperli, M., Pellaux, R., Heinemann, M. & Panke, S. Optimization of a blueprint for in vitro glycolysis by metabolic real-time analysis. Nat Chem Biol 7, 271-277, doi:10.1038/nchembio.541 (2011).

Tables

TABLE 1

Strains and Plasmids.

| Name | Genotype/relevant characteristics | Source |
|---|---|---|
| Strains | | |
| NEB Turbo ™ | F' proA+B+ lacIq ΔlacZM15/fhuA2 Δ(lac-proAB) glnV galK16 galE15 R(zgb-210::Tn10)TetS endA1 thi-1 Δ(hsdS-mcrB)5 | New England Biolabs |
| BL21 (DE3) | fhuA2 [lon] ompT gal (λ DE3) [dcm] ΔhsdS λ DE3 = λ sBamHIo ΔEcoRI-B int::(lacI::PlacUV5::T7 gene1) i21 Δnin5 | New England Biolabs |
| Strains & Plasmids | | |
| BL21 (DE3) pETBCS-rbsU-atoB | Strain used for protein production and extract preparation of AtoB | This Study |
| BL21 (DE3) pETBCS-rbsU-hbd1 | Strain used for protein production and extract preparation of Hbd1 | This Study |
| BL21 (DE3) pETBCS-rbsU-hbd2 | Strain used for protein production and extract preparation of Hbd2 | This Study |
| BL21 (DE3) pETBCS-rbsU-crt1 | Strain used for protein production and extract preparation of Crt1 | This Study |
| BL21 (DE3) pETBCS-rbsU-crt2 | Strain used for protein production and extract preparation of Crt2 | This Study |
| BL21 (DE3) pETBCS-rbsU-ter1 | Strain used for protein production and extract preparation of Ter1 | This Study |
| BL21 (DE3) pETBCS-rbsU-adhE1 | Strain used for protein production and extract preparation of AdhE1 | This Study |
| BL21 (DE3) pETBCS-rbsU-adhE2 | Strain used for protein production and extract preparation of AdhE2 | This Study |
| pJL1-atoB | Plasmid used for CFPS containing atoB | This Study |
| pJL1-hbd2 | Plasmid used for CFPS containing hbd2 | This Study |
| pJL1-crt1 | Plasmid used for CFPS containing crt1 | This Study |
| pJL1-ter1 | Plasmid used for CFPS containing ter1 | This Study |
| pJL1-adhE1 | Plasmid used for CFPS containing adhE1 | This Study |
| pJL1-hbdcrt2 | Plasmid used for CFPS containing hbdcrt2 | This Study |
| pJL1-hbdcrt3 | Plasmid used for CFPS containing hbdcrt3 | This Study |
| pJL1-hbdcrt4 | Plasmid used for CFPS containing hbdcrt4 | This Study |
| pJL1-hbdcrt6 | Plasmid used for CFPS containing hbdcrt6 | This Study |
| pJL1-ter3 | Plasmid used for CFPS containing ter3 | This Study |
| pJL1-ter4 | Plasmid used for CFPS containing ter4 | This Study |
| pJL1-ter5 | Plasmid used for CFPS containing ter5 | This Study |
| pJL1-ter6 | Plasmid used for CFPS containing ter6 | This Study |
| pJL1-adhE9 | Plasmid used for CFPS containing adhE9 | This Study |
| pJL1-adhE10 | Plasmid used for CFPS containing adhE10 | This Study |
| pJL1-adhE13 | Plasmid used for CFPS containing adhE13 | This Study |

TABLE 2

Genes and Enzymes.

| Gene/Enzyme | Enyme Activity | Source Organism | Source Database |
|---|---|---|---|
| atoB | acetyl-CoA acetyltransferase/thiolase | *Escherichia coli* | GenBank |

TABLE 2-continued

Genes and Enzymes.

| Gene/Enzyme | Enyme Activity | Source Organism | Source Database |
|---|---|---|---|
| hbd1 | acyl-CoA dehydrogenase | *Clostridium Acetobutylicum* | GenBank |
| hbd2 | acyl-CoA dehydrogenase | *Clostridium beijerinckii* | GenBank |
| crt1 | acyl-CoA dehydrogenase | *Clostridium Acetobutylicum* | GenBank |
| crt2 | acyl-CoA dehydrogenase | *Pseudomonas putida* | GenBank |
| hbdcrt2 | 3-hydroxyacyl-CoA dehydrogenase | *Aeropyrum camini* | NCBI BLAST Search of ADHE2 protein from *C. acetobutyllicum* |
| hbdcrt3 | 3-hydroxyacyl-CoA dehydrogenase | *Pyrobaculum aerophilum* | NCBI BLAST Search of ADHE2 protein from *C. acetobutyllicum* |
| hbdcrt4 | 3-hydroxyacyl-CoA dehydrogenase | *Sulfolobus islandicus* | NCBI BLAST Search of ADHE2 protein from *C. acetobutyllicum* |
| hbdcrt5 | 3-hydroxyacyl-CoA dehydrogenase | *Vulcanisaeta distributa* | NCBI BLAST Search of TER protein from *T. denticola* |
| hbdcrt6 | 3-hydroxybutyryl-CoA dehydrogenase | *Sulfolobus acidocaldarius* | NCBI BLAST Search of TER protein from *T. denticola* |
| ter1 | trans-2-enoyl-CoA reductase | *Treponema denticola* | GenBank |
| ter3 | trans-2-enoyl-CoA reductase | *Fibrobacter succinogenes* | NCBI BLAST Search of TER protein from *T. denticola* |
| ter4 | trans-2-enoyl-CoA reductase | *Flavobacterium johnsoniae* | NCBI BLAST Search of TER protein from *T. denticola* |
| ter5 | trans-2-enoyl-CoA reductase | *Spirochaeta bajacaliforniensis* | NCBI BLAST Search of TER protein from *T. denticola* |
| ter6 | trans-2-enoyl-CoA reductase | *Cytophaga hutchinsonii* | NCBI BLAST Search of HBD-CRT protein from *M. sedula* |
| adhE1 | bifunctional acetaldehyde-CoA/alcohol dehydrogenase | *Clostridium acetobutylicum* | GenBank |
| adhE2 | bifunctional acetaldehyde-CoA/alcohol dehydrogenase | *Clostridium pasteurianum* | NCBI BLAST Search of HBD-CRT protein from *M. sedula* |
| adhE8 | bifunctional acetaldehyde-CoA/alcohol dehydrogenase | *Chitinivibrio alkaliphilus* | NCBI BLAST Search of HBD-CRT protein from *M. sedula* |
| adhE9 | bifunctional acetaldehyde-CoA/alcohol dehydrogenase | *Thermosynechococcus* sp. NK55a | NCBI BLAST Search of HBD-CRT protein from *M. sedula* |
| adhE10 | bifunctional acetaldehyde-CoA/alcohol dehydrogenase | *Providencia burhodogranariea* | NCBI BLAST Search of HBD-CRT protein from *M. sedula* |
| adhE13 | bifunctional acetaldehyde-CoA/alcohol dehydrogenase | *Serratia marcescens* | NCBI BLAST Search of HBD-CRT protein from *M. sedula* |

It will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Citations to a number of patent and non-patent references are made herein. The cited references are incorporated by reference herein in their entireties. In the event that there is an inconsistency between a definition of a term in the specification as compared to a definition of the term in a cited reference, the term should be interpreted based on the definition in the specification.

What is claimed:

1. A method for the enzymatic preparation of 1-butanol or an intermediate of 1-butanol in the 1-butanol synthetic pathway in vitro from a feedstock comprising glucose or a product of glycolysis that reacts with one or more enzymes to produce the 1-butanol or the intermediate of 1-butanol in the 1-butanol synthetic pathway, the method comprising:

(a) reacting a cell-free protein synthesis reaction mixture, the cell-free protein synthesis reaction mixture comprising a cellular extract from a host strain, a translation template encoding the one or more enzymes, and cell-free protein synthesis reagents, (b) expressing the translation template in the cell-free protein synthesis reaction mixture to prepare the one or more enzymes, (c) combining the cell-free protein synthesis reaction mixture and a metabolic reaction mixture, the metabolic reaction mixture comprising the feedstock, wherein the feedstock reacts in the presence of the one or more enzymes to prepare the 1-butanol or the intermediate of 1-butanol in the 1-butanol synthetic pathway and wherein the cellular extract provides natural enzyme metabolism from the host strain;

wherein the one or more enzymes are selected from the group consisting of AtoB, Hbd, Crt, Ter, AdhE, and combinations thereof; and wherein the intermediate of 1-butanol in the 1-butanol synthetic pathway is selected from acetoacetyl-CoA, 3-hydroxybutyryl-CoA, crotonyl-CoA, butyryl-CoA, and butyraldehyde.

2. The method of claim 1, wherein the natural enzyme metabolism from the host strain (i) provides energy; (ii) provides cofactor regeneration; (iii) provides a cellular extract enzyme; or (iv) any combination thereof.

3. The method of claim 1, the method further comprising providing a transcription template, a polymerase, ATP, GTP, CTP, and UTP to prepare the translation template.

4. The method of claim 1, wherein the protein reaction vessel and the metabolic reaction vessel are different vessels.

5. The method of claim 1, wherein the protein reaction vessel and the metabolic reaction vessel are the same vessel.

6. The method of claim 1, wherein the cellular extract is a prokaryotic cellular extract.

7. The method of claim 1, wherein the enzyme prepared in step (b) is heterologous relative to the cellular extract.

8. The method of claim 1, wherein the cell-free protein synthesis reagents comprise a reaction buffer, amino acids, and a tRNA mixture.

9. The method of claim 1, wherein the cell-free protein synthesis reagents comprise CoA, ATP, NAD, NADH, NADP, NADPH, FMN, SAM, potassium, magnesium, ammonium, glutamate, acetate, or any combination thereof.

10. The method of claim 1, wherein the enzyme prepared in step (b) is selected from the group consisting of AtoB, Hbd, Crt, Ter, AdhE, and combinations thereof.

11. The method of claim 1, wherein the feedstock comprises glucose.

12. The method of claim 1, wherein the metabolic reaction mixture comprises CoA, malonyl-CoA, acetyl-CoA, 4'-phosphopantetheinyl transferase enzyme Sfp, ATP, NAD, NADH, NADP, NADPH, FMN, potassium, magnesium, ammonium, glutamate, acetate, any of the 20 amino acids, or any combinations thereof.

13. A method for the enzymatic preparation of 1-butanol in vitro from a feedstock that comprises glucose or products of glycolysis that reacts with one or more enzymes in the 1-butanol synthetic pathway to produce 1-butanol, the method comprising:

(a) reacting a cell-free protein synthesis reaction mixture, the cell-free protein synthesis reaction mixture comprising a cellular extract from a host strain of *E. coli*, a translation template encoding the one or more enzymes, and cell-free protein synthesis reagents, (b) expressing the translation template in the cell-free protein synthesis reaction mixture to prepare the one or more enzymes in the 1-butanol synthetic pathway, (c) combining the cell-free protein synthesis reaction mixture and a metabolic reaction mixture, the metabolic reaction mixture comprising the feedstock, wherein the feedstock reacts in the presence of the one or more enzymes in the in the 1-butanol synthetic pathway to prepare the 1-butanol and wherein the cellular extract provides natural enzyme metabolism from the host strain; and wherein the one or more enzymes are selected from the group consisting of AtoB, Hbd, Crt, Ter, AdhE, and combinations thereof.

14. The method of claim 13, wherein the natural enzyme metabolism from the host strain (i) provides energy; (ii) provides cofactor regeneration; (iii) provides a cellular extract enzyme; or (iv) any combination thereof.

15. The method of claim 13, the method further comprising providing a transcription template, a polymerase, ATP, GTP, CTP, and UTP to prepare the translation template.

16. The method of claim 13, wherein the enzyme prepared in step (b) is heterologous relative to the cellular extract.

\* \* \* \* \*